United States Patent
Chen et al.

(10) Patent No.: US 9,896,485 B2
(45) Date of Patent: Feb. 20, 2018

(54) NANOPORE SENSORS AND USES THEREOF

(71) Applicant: University of Massachusetts, Boston, MA (US)

(72) Inventors: Min Chen, Amherst, MA (US); Christina Chisholm, Sunderland, MA (US); Monifa A. V. Fahie, Amherst, MA (US)

(73) Assignee: University of Massachusetts, Boston, MA (US)

( * ) Notice: Subject to any disclaimer, the term of this patent is extended or adjusted under 35 U.S.C. 154(b) by 236 days.

(21) Appl. No.: 14/338,316

(22) Filed: Jul. 22, 2014

(65) Prior Publication Data
US 2015/0080242 A1    Mar. 19, 2015

Related U.S. Application Data

(60) Provisional application No. 61/856,814, filed on Jul. 22, 2013.

(51) Int. Cl.
C40B 40/10  (2006.01)
C07K 14/245  (2006.01)
G01N 33/487  (2006.01)

(52) U.S. Cl.
CPC ............ *C07K 14/245* (2013.01); *C40B 40/10* (2013.01); *G01N 33/48721* (2013.01); *G01N 2333/245* (2013.01)

(58) Field of Classification Search
None
See application file for complete search history.

(56) References Cited

PUBLICATIONS

Chen et al., Orientation of the monomeric porin OmpG in planar lipid bilayers. Chembiochem. Dec. 15, 2008;9(18):3029-36. doi: 10.1002/cbic.200800444.
Chen et al., Outer membrane protein G: Engineering a quiet pore for biosensing. Proc Natl Acad Sci U S A. Apr. 29, 2008;105(17):6272-7. doi: 10.1073/pnas.0711561105. Epub Apr. 28, 2008.
Fahie et al., A non-classical assembly pathway of *Escherichia coli* pore-forming toxin cytolysin A. J Biol Chem.Oct. 25, 2013;288(43):31042-51. doi: 10.1074/jbc.M113.475350. Epub Sep. 9, 2013.
Zhuang et al., NMR-based conformational ensembles explain pH-gated opening and closing of OmpG channel. J Am Chem Soc. Oct. 9, 2013;135(40):15101-13. doi: 10.1021/ja408206e. Epub Oct. 1, 2013.

*Primary Examiner* — Christian Boesen
(74) *Attorney, Agent, or Firm* — Wolf, Greenfield & Sacks, P.C.

(57) ABSTRACT

Aspects of the invention relate to nanopores useful as sensors for detecting intermolecular interactions.

8 Claims, 22 Drawing Sheets

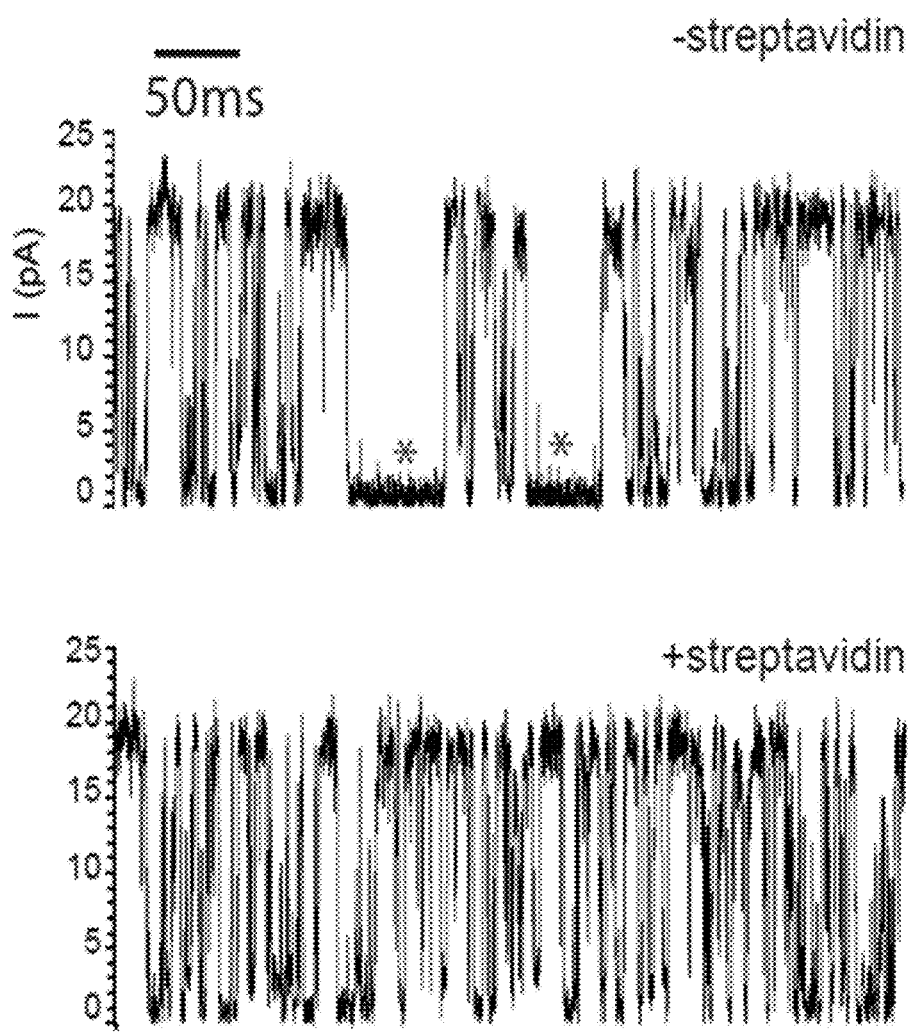

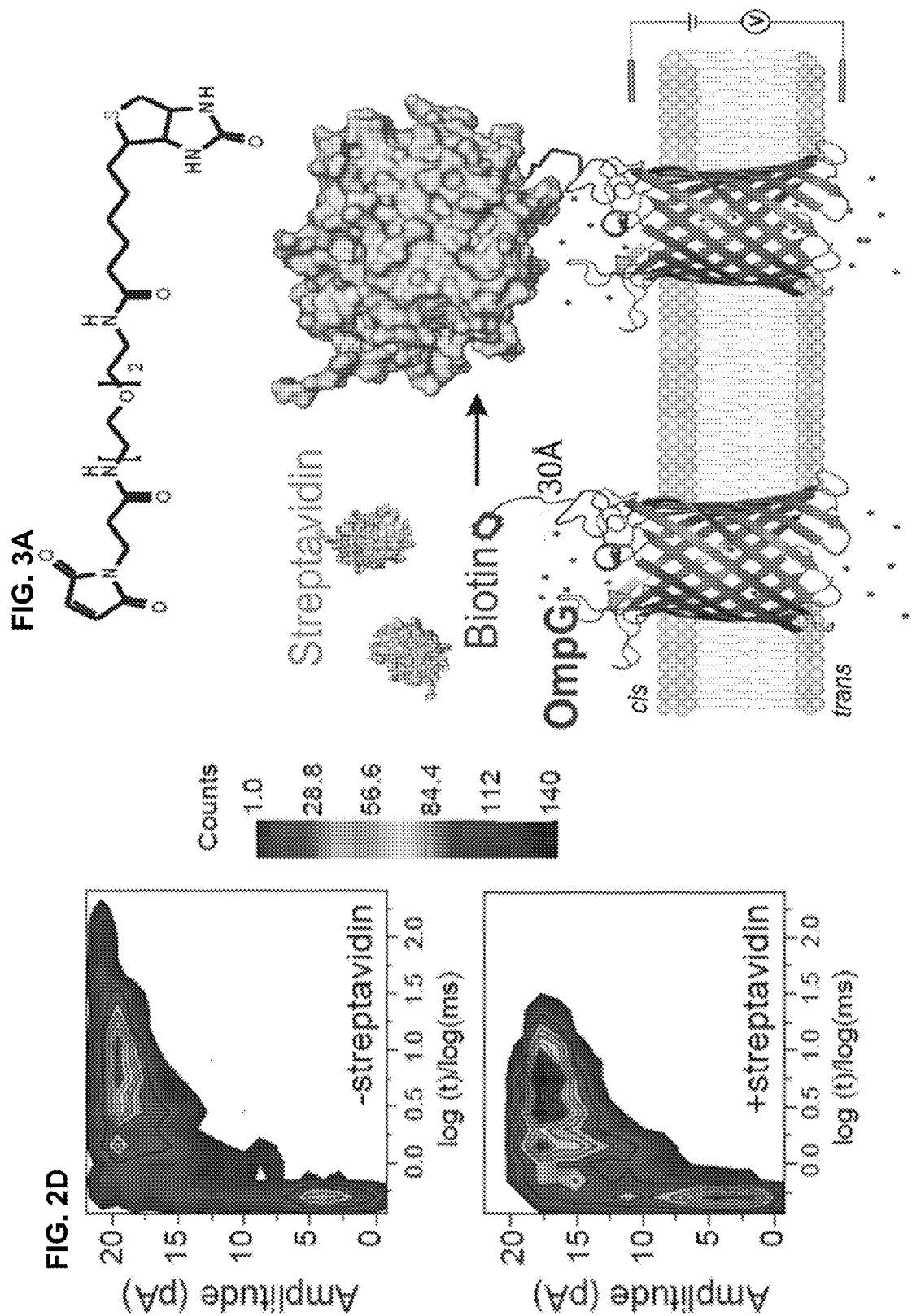

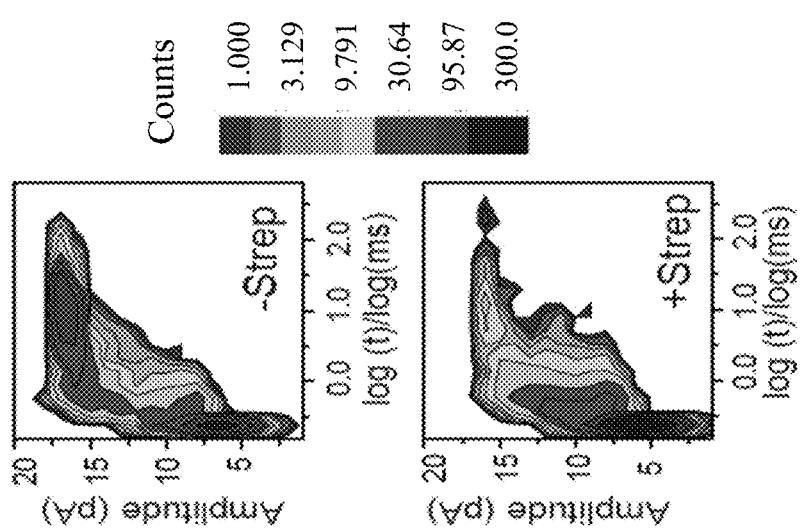
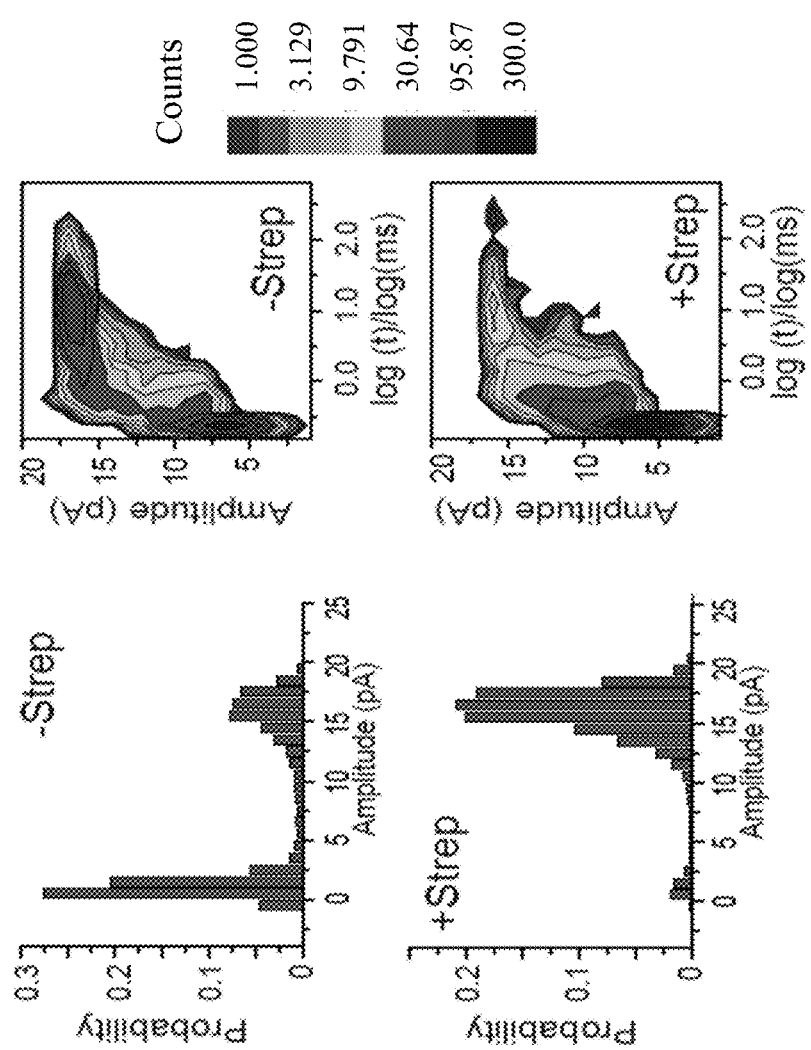
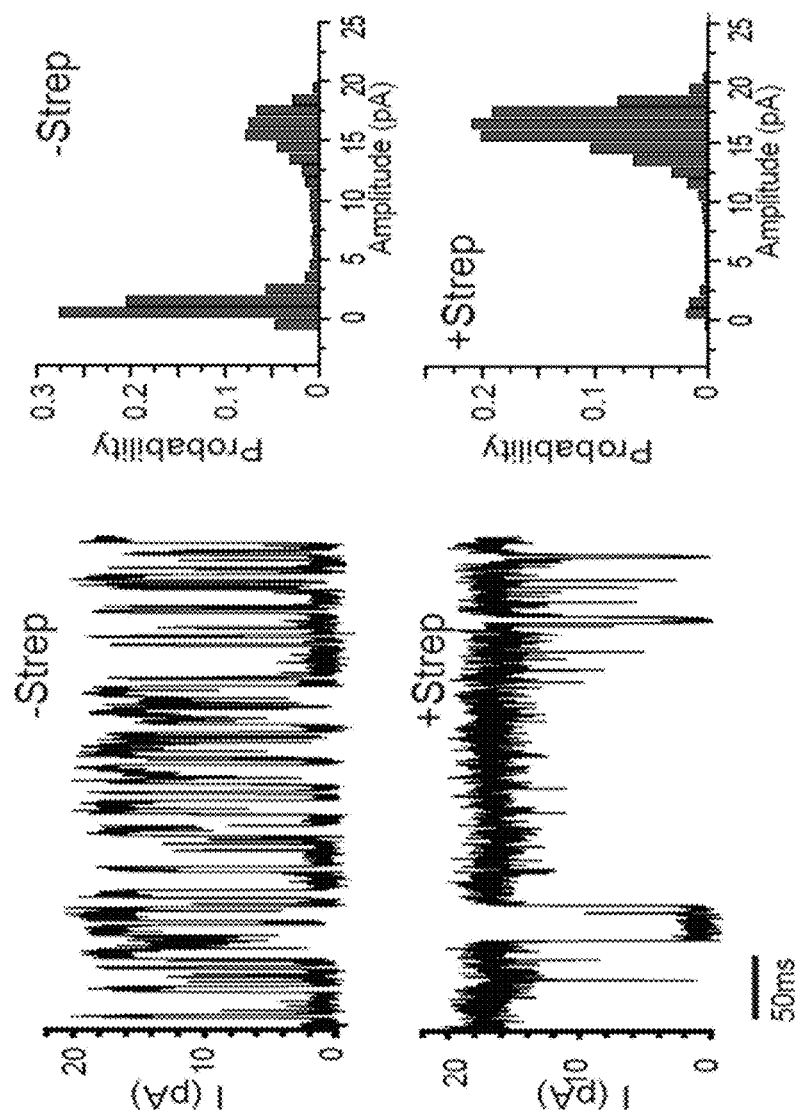
FIG. 3B
FIG. 3C
FIG. 3D

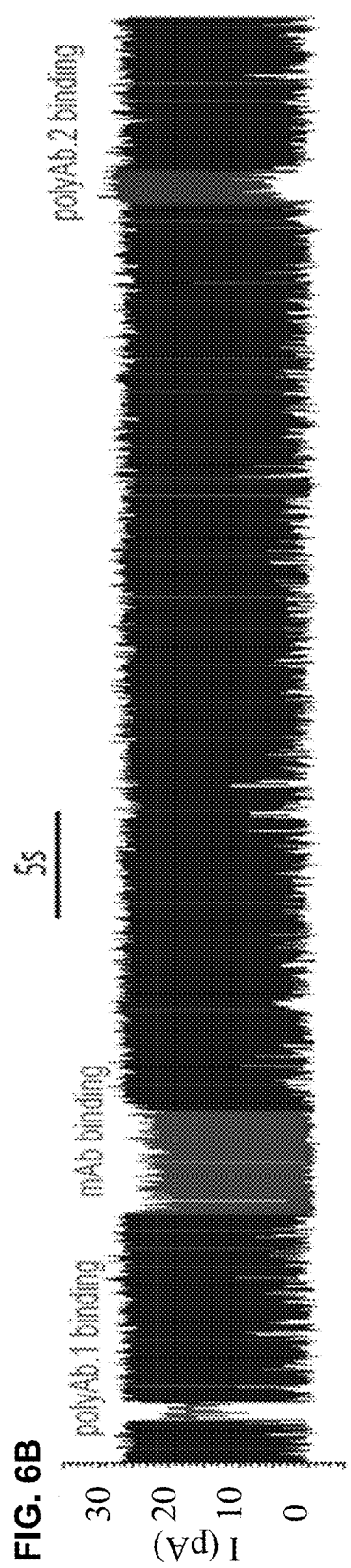

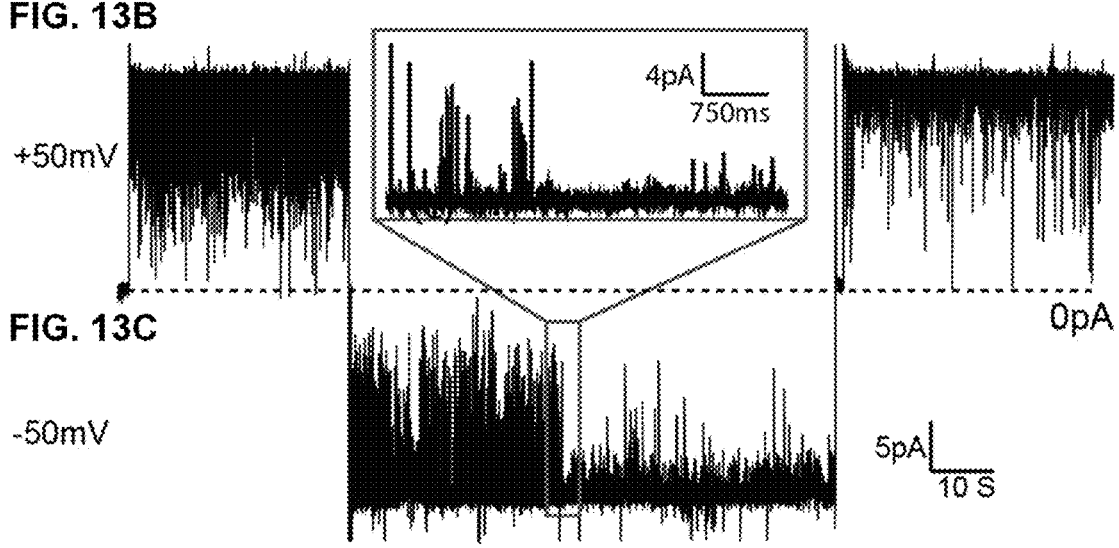
FIG. 13B
FIG. 13C
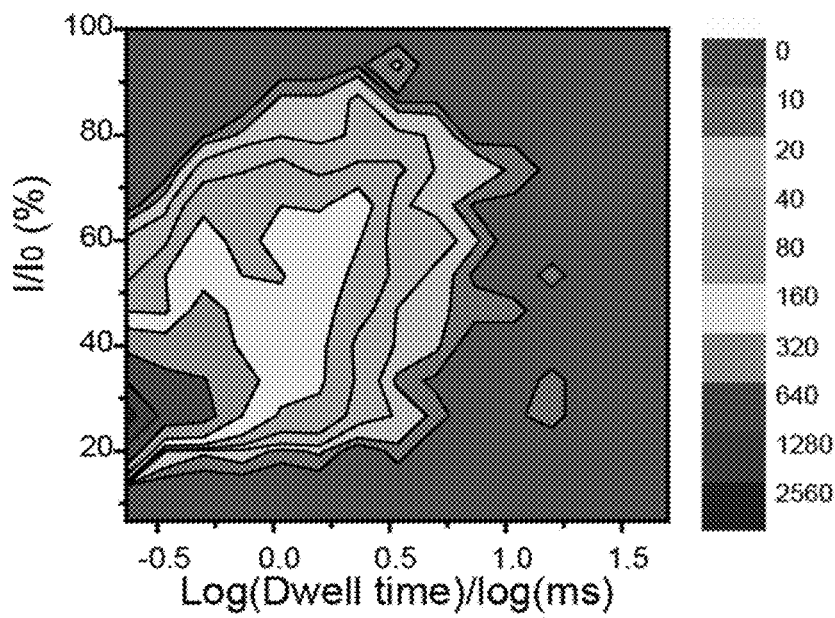
FIG. 13D

```
                              SEQUENCE LISTING

<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 1
gggactggca gtgtgatatt gaacgtgaag                                         30

<210> SEQ ID NO 2
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 2
gttcaatatc acactgccag tcccagttac                                         30

<210> SEQ ID NO 3
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 3
cagaagtggt cctgcaactt tatc                                               24

<210> SEQ ID NO 4
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 4
ataaagttgc aggaccactt ctg                                                23

<210> SEQ ID NO 5
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 5

Gly Glu Glu Arg Asn Asp Trp His Phe Asn Ile Gly Ala Met Tyr Glu
```

```
            1               5                  10                 15
        Ile Glu Asn Val Glu Gly Tyr Gly Glu Asp Met Asp Gly Leu Ala Glu
                        20                 25                 30

Pro Ser Val Tyr Phe Asn Ala Ala Asn Gly Pro Trp Arg Ile Ala Leu
                        35                 40                 45

Ala Tyr Tyr Gln Glu Gly Pro Val Asp Tyr Ser Ala Gly Lys Arg Gly
                        50                 55                 60

Thr Trp Phe Asp Arg Pro Glu Leu Glu Val His Tyr Gln Phe Leu Glu
        65                  70                 75                 80

Asn Asp Asp Phe Ser Phe Gly Leu Thr Gly Gly Phe Arg Asn Tyr Gly
                        85                 90                 95

Tyr His Tyr Val Asp Glu Pro Gly Lys Asp Thr Ala Asn Met Gln Arg
                        100                105                110

Trp Lys Ile Ala Pro Asp Trp Asp Val Lys Leu Thr Asp Asp Leu Arg
                        115                120                125

Phe Asn Gly Trp Leu Ser Met Tyr Lys Phe Ala Asn Asp Leu Asn Thr
                        130                135                140

Thr Gly Tyr Ala Asp Thr Arg Val Glu Thr Glu Thr Gly Leu Gln Tyr
        145                 150                155                160

Thr Phe Asn Glu Thr Val Ala Leu Arg Val Asn Tyr Tyr Leu Glu Arg
                        165                170                175

Gly Phe Asn Met Asp Asp Ser Arg Asn Asn Gly Glu Phe Ser Thr Gln
                        180                185                190

Glu Ile Arg Ala Tyr Leu Pro Leu Thr Leu Gly Asn His Ser Val Thr
                        195                200                205

Pro Tyr Thr Arg Ile Gly Leu Asp Arg Trp Ser Asn Trp Asp Trp Gln
                        210                215                220

Asp Asp Ile Glu Arg Glu Gly His Asp Phe Asn Arg Val Gly Leu Phe
        225                 230                235                240

Tyr Gly Tyr Asp Phe Gln Asn Gly Leu Ser Val Ser Leu Glu Tyr Ala
                        245                250                255

Phe Glu Trp Gln Asp His Asp Glu Gly Asp Ser Asp Lys Phe His Tyr
                        260                265                270

Ala Gly Val Gly Val Asn Tyr Ser Phe
                        275                280

<210> SEQ ID NO 6
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 6

Gly Glu Glu Arg Asn Asp Trp His Phe Asn Ile Gly Ala Met Tyr Glu
        1               5                  10                 15

Ile Glu Asn Val Glu Gly Tyr Gly Glu Asp Met Asp Gly Leu Ala Glu
                        20                 25                 30

Pro Ser Val Tyr Phe Asn Ala Ala Asn Gly Pro Trp Arg Ile Ala Leu
                        35                 40                 45

Ala Tyr Tyr Gln Glu Gly Pro Val Asp Tyr Ser Ala Gly Lys Arg Gly
                        50                 55                 60

Thr Trp Phe Asp Arg Pro Glu Leu Glu Val His Tyr Gln Phe Leu Glu
        65                  70                 75                 80

Asn Asp Asp Phe Ser Phe Gly Leu Thr Gly Gly Phe Arg Asn Tyr Gly
```

```
                    85                  90                  95
Tyr His Tyr Val Asp Glu Pro Gly Lys Asp Thr Ala Asn Met Gln Arg
                100                 105                 110

Trp Lys Ile Ala Pro Asp Trp Asp Val Lys Leu Thr Asp Asp Leu Arg
            115                 120                 125

Phe Asn Gly Trp Leu Ser Met Tyr Lys Phe Ala Asn Asp Leu Asn Thr
        130                 135                 140

Thr Gly Tyr Ala Asp Thr Arg Val Glu Thr Glu Thr Gly Leu Gln Tyr
145                 150                 155                 160

Thr Phe Asn Glu Thr Val Ala Leu Arg Val Asn Tyr Tyr Leu Glu Arg
                165                 170                 175

Gly Phe Asn Met Asp Asp Ser Arg Asn Asn Gly Glu Phe Ser Thr Gln
                180                 185                 190

Glu Ile Arg Ala Tyr Leu Pro Leu Thr Leu Gly Asn His Ser Val Thr
                195                 200                 205

Pro Tyr Thr Arg Ile Gly Leu Asp Arg Trp Ser Asn Trp Asp Trp Gln
            210                 215                 220

Cys Asp Ile Glu Arg Glu Gly His Asp Phe Asn Arg Val Gly Leu Phe
225                 230                 235                 240

Tyr Gly Tyr Asp Phe Gln Asn Gly Leu Ser Val Ser Leu Glu Tyr Ala
                245                 250                 255

Phe Glu Trp Gln Asp His Asp Glu Gly Asp Ser Asp Lys Phe His Tyr
                260                 265                 270

Ala Gly Val Gly Val Asn Tyr Ser Phe
            275                 280

<210> SEQ ID NO 7
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 7

Ser Asn Trp Asp Trp Gln Asp Asp Ile Glu Arg Glu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

Ser Asn Trp Asp Trp Gln Cys Asp Ile Glu Arg Glu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 9

Ser Asn Trp Cys Trp Gln Asp Asp Ile Glu Arg Glu
1               5                   10
```

NANOPORE SENSORS AND USES THEREOF

RELATED APPLICATIONS

This application claims priority under 35 U.S.C. §119(e) to U.S. Provisional Application Ser. No. 61/856,814, entitled "NANOPORE SENSORS AND USES THEREOF" filed on Jul. 22, 2013, which is herein incorporated by reference in its entirety.

BACKGROUND

Nanopores have been used in label-free single-molecule studies, including investigations of chemical reactions, nucleic acid analysis, and applications in sensing. Nanopores are powerful single-molecule analytical tools that enable the study of fundamental problems in chemistry and biology, including, for example, protein folding, enzymatic activity, and chemical reactions. Beyond basic research, nanopores are useful in various biotech applications, such as DNA sequencing and biosensing.

SUMMARY OF INVENTION

Aspects of the invention relate to nanopores useful as sensors for detecting intermolecular interactions. In some embodiments, nanopores are provided that can be used as sensors in diagnosis of diseases and/or infections (e.g., bacterial or viral infections). In some embodiments, nanopores are provided that can be used as sensors in war fields or other situations for rapid-detection of biological weapons. In some embodiments, nanopores are provided that can be used as sensors for rapid-detection of biological contaminants in the environment. In some embodiments, nanopores are provided that can be used as sensors for detection of large biological molecules, such as nucleic acids, proteins, virus, bacteria, etc. In some embodiments, changes in dynamic movement of loops of a nanopore (e.g., a β-barrel protein nanopore) upon target analyte binding provide a basis for sensing. In some embodiments, high-affinity binding sites are engineered into loops of a nanopore for sensing target molecules. In some embodiments, a library of nanopores is provided in which the nanopores in the library contain loops with randomized sequences for rapid-selection of suitable biosensors to detect specific targets.

Aspects of the invention relate to methods of detecting binding of a ligand to a target. In some embodiments, methods provided herein involve exposing a nanopore to a target, in which the nanopore is disposed in a membrane preparation, and in which the nanopore is associated with a ligand; assessing a gating pattern of the nanopore; and detecting binding of the ligand to the target based on the gating pattern.

In some embodiments, the target is a protein. In some embodiments, the target is a virus or bacteria. In some embodiments, the target is a nucleic acid. In some embodiments, the target is a biological cell, such as a bacterium or eukaryotic cell. In certain embodiments, the target is immobilized.

In some embodiments, the nanopore is covalently linked to the ligand. In certain embodiments, the nanopore is covalently linked to the ligand directly. In some embodiments, the nanopore is covalently linked to the ligand via a linker molecule. In certain embodiments, the linker molecule is comprises polyethylene or other another molecule. In some embodiments, the nanopore comprises, as the ligand, a high-affinity peptide that binds to the target. In certain embodiments, the high-affinity peptide is incorporated into an exposed loop of the nanopore.

In some embodiments, the nanopore is a monomeric protein nanopore. In certain embodiments, the nanopore comprises a plurality of β-strands connected by a plurality of flexible loops of a first side of the membrane preparation and a plurality of short turns on a second side of the membrane preparation. In some embodiments, the nanopore comprises 8 to 22 β-strands connected by flexible loops on a first side of the membrane preparation and a plurality of short turns on a second side of the membrane preparation. In certain embodiments, the nanopore comprises 14 β-strands connected by seven flexible loops on a first side of the membrane preparation and seven short turns on a second side of the membrane preparation. In some embodiments, the nanopore comprises on the first side an opening in a range of 6 to 10 Å in diameter and an opening on the second side in a range of 12 to 16 Å. In certain embodiments, at least one of the flexible loops of the nanopore is mutated to modulate gating characteristics of the nanopore. In certain embodiments, a nanopore has a stabilizing mutation in a beta-barrel region. In certain embodiments, at least one of the flexible loops of the nanopore is stabilized to reduce gating. In certain embodiments, at least one of the flexible loops of the nanopore is mutated to increase its flexibility. In some embodiments, the nanopore is an outer membrane protein G composed of 14 β-strands connected by seven flexible loops on the extracellular side and seven short turns on the periplasmic side, and wherein loop 6 is stabilized to an open conformation to reduce gating. In certain embodiments, the ligand is covalently linked to loop 6 of the nanopore. In some embodiments, the nanopore is an outer membrane protein G (OmpG). In certain embodiments, the OmpG is of *E. coli* origin. In some embodiments, the nanopore is a pore from a mitochondria membrane. In certain embodiments, the nanopore is a synthetic peptide or polymer that forms a pore in a membrane. In some embodiments, the nanopore spontaneously gates in the membrane preparation during an applied potential.

In some embodiments, binding of a ligand to target results in a conformational change in the nanopore that alters ion current flow through the pore. In some embodiments, the change in ion current flow is a result of a change in gating due to the conformational change. In some embodiments, the nanopore detects target binding in a manner that does not involve entry of the target into the pore lumen.

In certain embodiments, determining the gating pattern comprises performing a single channel recording of ion flow through the nanopore. In some embodiments, the single channel recording is performed while exposing the nanopore to a potential in a range of −250 to +250 mV or −100 to +100 mV. In certain embodiments, the single channel recording is performed while exposing the nanopore to a potential in a range of −50 mV to +50 mV. In some embodiments, binding of the ligand to the target molecule is detected based on an alteration (e.g., an increase or a reduction) in the gating pattern resulting from exposing the nanopore to a target molecule. In some embodiments, binding of the ligand to the target molecule is detected based on an alteration (e.g., an increase or a reduction) in amplitude and/or frequency of gating. In some embodiments, alterations in gating patterns are due to the interaction of bound analyte with one or more loops at the ligand side of a beta barrel of a nanopore. In some embodiments, an analyte can slow down or otherwise alter the movement of a loop, e.g., by containing or tethering the loop, or altering the loop such that it is stuck in a "half-open" or "closed" position, etc.

In certain embodiments, the reduction is a reduction of the frequency and/or amplitude of gating events. In some embodiments, determining the gating pattern comprises determining a gating frequency (f, events/s). In certain embodiments, the gating frequency is a relationship between a total number of gating events and a recording time. In some embodiments, determining the gating pattern comprises determining a gating probability (Pgating). In certain embodiments, the gating probability is a relationship between a total time for which a pore is in a closed or partially closed state and a total recording time (total open and closed time). In some embodiments, determining the gating pattern comprises determining loop dynamics to detect ligand-target interactions. In some embodiments, a gating pattern change is from "quiet" to "noisy". However, in some embodiments, a gating pattern change is from noisy to quiet. In some embodiments, a reduction is gating pattern from noisy to quiet occurs where a reduction in the ionic current noise is greater than 10%.

In certain embodiments, the membrane preparation is a synthetic membrane preparation. In some embodiments, the membrane preparation is a planar lipid bilayer. In certain embodiments, the membrane preparation is a micelle. In some embodiments, the membrane preparation is a membrane of a biological cell. In certain embodiments, the biological cell is a bacterium. In some embodiments, the biological cell is a eukaryotic cell.

According to some aspects of the invention compositions are provided. In some embodiments, the compositions comprise: an outer membrane protein disposed in a membrane preparation, the outer membrane protein comprising a plurality of β-strands connected by a plurality of flexible loops on a first side of the membrane preparation and a plurality of short turns on a second side of the membrane preparation, in which at least one of the flexible loops comprises an engineered binding site for a target molecule; and the target molecule.

According to some aspects of the invention a collection of engineered outer membrane proteins is provided. In some embodiments, each outer membrane protein in the collection, when disposed in a membrane preparation, comprises a plurality of β-strands connected by a plurality of flexible loops on a first side of the membrane preparation and a plurality of short turns on a second side of the membrane preparation, in which at least one of the flexible loops comprises an engineered binding site; and in which the engineered binding site of each outer membrane in the collection is different than the engineered binding site of each other outer membrane protein in the collection. In some embodiments, each of the engineered outer membrane proteins is disposed in the outer membrane of a different bacterium. In some embodiments, each of the engineered outer membrane proteins is housed in a different container.

According to some aspects of the invention a collection of engineered outer membrane proteins, in which the engineered outer membrane proteins are disposed in a membrane preparation such that on one side of the membrane preparation the engineered outer membrane proteins are exposed to a common chamber and on the other side of the membrane preparation each engineered outer membrane protein is exposed to a separate chamber. In some embodiments, the extracellular loop of each engineered outer membrane protein is exposed to the common chamber. In some embodiments, the extracellular loop of each engineered outer membrane protein is exposed to the separate chamber. In some embodiments, the collection of engineered outer membrane proteins is configured for multi-nanopore high-throughput measurements. In some embodiments, a set of multiple nanopore is provided in a membrane preparation (e.g., in a 2-dimensional array) such that at one side of the membrane preparation the multiple nanopores are exposed to a single chamber, and at the other side of the membrane preparation, each nanopore is exposed to an individual chamber.

In some embodiments, a nucleic acid is provided that encodes an engineered outer membrane protein disclosed herein. According to some aspects of the invention a collection of nucleic acids is provided, in which each nucleic acid encodes an engineered outer membrane protein disclosed herein.

According to some aspects of the invention methods of identifying a binding site of a target are provided. In some embodiments, the methods involve obtaining a collection of engineered outer membrane proteins, in which each outer membrane protein is disposed in a membrane preparation and comprises a plurality of β-strands connected by a plurality of flexible loops on a first side of the membrane preparation and a plurality of short turns on a second side of the membrane preparation, in which at least one of the flexible loops comprises an engineered binding site, and in which the engineered binding site of each outer membrane in the collection is different than the engineered binding site of each other outer membrane protein in the collection; exposing each of the engineered outer membrane proteins of the collection to a target; isolating an engineered outer membrane protein of the collection that binds to the target; and determining the amino acid sequence of the engineered binding site of the isolated outer membrane protein, thereby identifying a binding site of the target. In some embodiments, the engineered binding site is generated by randomized mutagenesis of the at least one flexible loop. In some embodiments, the target is immobilized.

According to some aspects of the invention methods of detecting binding of a ligand to a target are provided that comprise exposing a nanopore to a target, wherein the nanopore is disposed in a membrane preparation, and wherein the nanopore is associated with a ligand; assessing ion current flow through the nanopore; and detecting binding of the ligand to the target based on the ion current flow. In some embodiments, ligand-target binding is indicated by a block in ion current flow.

BRIEF DESCRIPTION OF DRAWINGS

FIG. 1A shows the structural alignment of the open and closed states of OmpG. Loop 6 in the open state is shown to the right of the figure and is found to the left of the figure in the closed state. The D224C mutation is shown in ball and stick model. FIG. 1B shows Single channel recording trace of a wild type OmpG pore. The data was obtained in buffer 10 mM Tris, pH 8.0, 150 mM KCl at +50 mV;

FIGS. 2A-D show the detection of streptavidin by OmpG-PEG$_{11}$-biotin pore. FIG. 2A depicts the schematic model showing the OmpG nanopore chemically modified with maleimide-PEG$_{11}$-biotin. The model was generated in Pymol using PDB files of OmpG (2IWV) and streptavidin (3RY1). The streptavidin was placed approximately 70 Å away from the OmpG pore in the model of the bound state. FIG. 2B shows the Representative traces of the OmpG pores before and after the addition of the streptavidin (3 nM). The measurements were performed in buffer 10 mM Na2PO4, pH6.0, 150 mM KCl at +50 mV. The gating event frequency increases from 75 s$^{-1}$ to 97 s$^{-1}$ after the addition of streptavidin. FIG. 2C shows all current histograms of the corresponding traces in FIG. 2B. FIG. 2D depicts two dimensional histograms of the gating events. Gating events collected from a 15 s recording trace were distributed based on their intensity versus duration. The color scale indicates the number of the events;

FIGS. 3A-3D depict the detection of streptavidin by OmpG-PEG$_2$-biotin pore. FIG. 3A shows a schematic model showing the OmpG nanopore chemically modified with a maleimade-PEG$_2$-biotin. The streptavidin is placed around 30 Å away from the OmpG pore in the model of the bound state. FIG. 3B shows a representative single channel recording traces of the OmpG pores before and after the addition of the streptavidin (3 nM). The measurements were performed in buffer 10 mM Na2PO4, pH 6.0, 150 mM KCl at +50 mV. FIG. 3C shows all current histograms of the corresponding traces in FIG. 3B. FIG. 3D shows two dimensional histograms of the gating events. Total number of 4000 gating events collected from ~220 s and ~40 s recording traces of OmpG pore with and without streptavidin bound were distributed based on their intensity versus duration. The gray scale indicates the number of the events;

FIG. 4A shows a schematic model showing the reversible binding of monoclonal anti-biotin antibody to OmpG-PEG$_2$-Biotin pore. The model is generated in Pymol using pdb files of OmpG (2IWV) and a mouse monoclonal anti-phenobarbital antibody (1IGY). The antibody was placed approximately 30 Å away from the OmpG pore in the captured model. FIG. 4B shows a representative single channel recording traces at various mAb concentrations. The mAb binding regions in the recording traces are highlighted in red. Increase of the mAb binding frequency was observed with increasing concentration of mAb. The measurements were performed in buffer 10 mM Na$_2$PO$_4$, pH 6.0, 300 M KCl at +50 mV. FIG. 4C shows all current histogram of the corresponding traces in FIG. 4B. The gray dashed lines from right to left emphasize the shift of the fully open states in current at unoccupied and mAb bound states respectively. FIGS. 4D and 4E show the concentration dependence of the $1/\tau_{off}$ and $1/\tau_{on}$, respectively. Error bars represent the standard deviations from the measurements of at least three independent pores;

FIG. 5A shows a representative single channel recording trace of OmpG-PEG$_2$-biotin showing reversible binding of the mAb at both +50 mV and −50 mV. The positive potential is defined as the potential of the chamber where the loops are located is positive as indicated in FIG. 4A. The measurement was performed in buffer, 10 mM sodium phosphate buffer, pH 6.0, 300 mM KCl in the presence of 10 nM mAb. FIG. 5B shows the representative single channel recording traces of OmpG-PEG$_2$-biotin at the unoccupied or mAb bound states at +50 mV and −50 mV. All current histograms of the corresponding current recording traces are also shown. The gray dashed lines from right to left emphasize the shift of the fully open states in current at unoccupied and mAb bound states respectively. The positive potential caused a larger shift of the open state current than the negative potential. FIGS. 5C and 5D show the voltage independence of $1/\tau_{on}$ and $1/\tau_{off}$. The measurements were performed in buffers 10 mM sodium phosphate buffer, pH 6.0, 300 mM KCl in the presence of 10 nM mAb at various applied voltages ranging from −50 mV to +50 mV;

FIGS. 6A-6D shows the stochastic detection of mouse mAb and polyclonal Ab binding by OmpG-PEG$_2$-biotin pore. FIG. 6A depicts a schematic model of simultaneous detection of multiple target proteins by OmpG nanopore. FIG. 6B shows the representative current trace of a single OmpG-biotin. The measurement was performed in the presence of mouse mAb (1 nM) and goat pAb (7.2 nM) in 10 mM Na2PO4, pH 6.0, 300 mM KCl at applied potential of +50 mV. The mAb and polyAb binding events can be found in the gray labeled sections of the figure. FIG. 6C shows the representative current recording trace of OmpG-PEG$_2$-biotin pore at the unoccupied and mAb and polyAb bound states. FIG. 6D shows all current histograms of the corresponding current recording traces;

FIGS. 13A-13D depict the detection of streptavidin by OmpG-biotin. FIG. 13A shows single channel recording trace of the OmpG proteins. The buffer used was 25 mM Tris, pH 7.0, 0.15 M KCl. FIGS. 13B and 13C show a comparison of gating activities of wild-type OmpG and OmpG biotin before and after streptavidin binding. Binding of the streptavidin induced the gating pattern change which was highlighted in the boxes connecting FIG. 13B and FIG. 13C. The relative gating frequency f and P$_{gating}$ of OmpG proteins are calculated taking the f and P$_{gating}$ of wild-type OmpG as 100%. FIG. 13D shows 2-dimentional event distribution plots associated with OmpG-biotin before and after streptavidin binding. The distribution of gating events from 10 min recording time is plotted according to the event amplitudes and dwell times. The amplitude (I) is the current change of an event relative to the current at the fully open state (I0)

DETAILED DESCRIPTION OF INVENTION

Figure 1A:
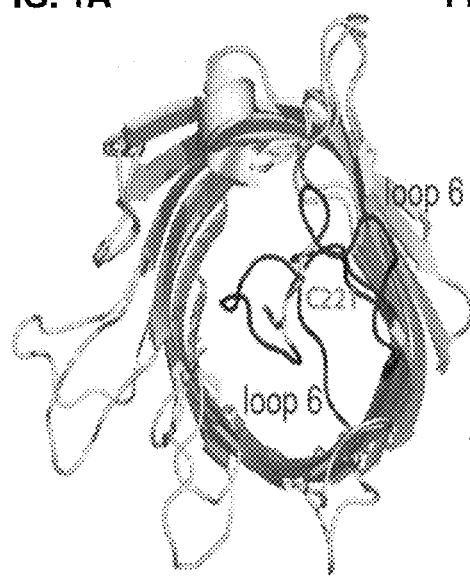
FIGS. 1A and 1B show structures of OmpG and its gating activity.

Aspects of the invention relate to nanopores useful as sensors for detecting intermolecular interactions. According to some aspects of the invention, nanopore sensing is based on reading ionic current passing through an individual protein or synthetic nano-sized pore. In some embodiments, the interaction between analytes and the sensor pore alters ionic current. Accordingly, in some embodiments, information about the identity of analytes, as well as their concentrations may be gathered. In some embodiments, nanopore sensing is sensitive (nanomolar concentrations), fast (up to microsecond resolution), and without delays from mixing and diffusion (real-time). In some embodiments, molecular detection using a single nanopore works by observing modulations in ionic current flowing through the pore during an applied potential.

In some aspects of the disclosure oligomeric protein nanopores with rigid structures have been engineered that are useful for sensing a wide range of analytes including small molecules and biological species such as proteins and DNA. In some embodiments, a monomeric β-barrel porin, OmpG, was selected as a platform from which to derive a nanopore sensor. In some embodiments, OmpG is decorated with several flexible loops that move dynamically to create a distinct gating pattern when ionic current passes through the pore. In some embodiments, biotin was chemically tethered to the most flexible one of these loops. In some embodiments, the gating characteristic of the loop's movement in and out of a porin was substantially altered by analyte protein binding. In some embodiments, the gating characteristics of the pore with bound targets were remarkably sensitive to molecular identity. In some embodiments, gating characteristics of the pore with bound targets provided the ability to distinguish between homologues within an antibody mixture. In some embodiments, a multiple gating parameters (e.g., five parameters) were analyzed for each of a number of analytes to create a unique fingerprint for each binding molecule (e.g., biotin binding protein). In some embodiments, exploitation of gating noise as a molecular identifier is advantageous because it enables sophisticated sensor designs and applications.

In some embodiments, bacterial outer membrane porins, having robust β-barrel structures, are used as stochastic sensors based on single-molecule detection. For example, in some embodiments, OmpG's monomeric structure greatly simplifies nanopore production. In some embodiments, a monomeric porin, OmpG, is advantageous as a nanopore because appropriate modifications of the pore can be easily achieved by mutagenesis. In some embodiments, gating of a nanopore causes transient current blockades in single-channel recordings that may interfere with analyte detection. Thus, in some embodiments, to control spontaneous gating activity, approaches were used to enhance the stability of the open conformation by site-directed mutagenesis. In some embodiments, binding of an analyte to a nanopore partially blocks the flow of current and provides information about a molecules size, concentration and affinity. In some embodiments, direct protein detection with nanopores does not involve transmitting a binding signal from solution to a pore interior.

For example, mobility of loop 6 of OmpG was reduced by introducing a disulfide bond between the extracellular ends of strands 12 and 13. In some embodiments, interstrand hydrogen bonding between strands 11 and 12 was optimized by deletion of residue D215 of OmpG. In some embodiments, an OmpG porin with both stabilizing mutations exhibited a 95% reduction in gating activity. This mutant OmpG was used for the detection of adenosine diphosphate at the single-molecule level, after equipping the porin with a cyclodextrin molecular adapter, thereby demonstrating its potential for use in stochastic sensing applications. To expand utility of the OmpG sensor, a strategy was developed to detect large biological molecules outside of the OmpG lumen. In some embodiments, a ligand was covalently attached on loop 6 of OmpG to fish for the target protein. In some embodiments, protein binding to the ligand altered the dynamics of loop 6 and causes a significant change in the gating pattern of the current recording. This approach is applicable for detection of any protein or other targets with a high-affinity ligand.

In some embodiments, methods are provided herein that use loop dynamics rather than direct pore blockage to detect protein interactions. In some embodiments, a nanopore is provided herein that is based on the outer membrane protein G (OmpG) from $E.\ coli$. In some embodiments, the OmpG is composed of 14 β-strands connected by seven flexible loops on the extracellular side and seven short turns on the periplasmic side. In some embodiments, the extracellular opening is 8 Å in diameter and the periplasmic side is 14 Å. In some embodiments, the wild-type OmpG spontaneously gates during an applied potential as revealed by planar bilayer studies. In some embodiments, pore gating is attributed to loop 6 which flops in and out of the pore, intermittently blocking the current (FIG. 1). OmpG from $E\ coli$ and other species is monomeric. Thus, in some embodiments, complex and asymmetric alterations by chemical or genetic modifications are straightforward, making it an advantageous nanopore platform for developing sensing technology.

In some embodiments, detection of streptavidin is accomplished using biotin as a ligand. However it should be appreciated that other ligands, such as small nature or synthetic chemicals, nucleic acids, small peptides and saccharides can be applied to fish for target molecules.

In some embodiments, a ligand is covalently linked to a nanopore via a linker. In some embodiments, it has been demonstrated that a ligand can be tethered to a nanopore by a linker containing two-units of polyethylene. However, it should be appreciated that linkers with other chemical composition and varied length may also be used for purposes of tethering ligands. Furthermore, in some embodiments, ligands need not be tethered to nanopores. For example, a ligand may be incorporated directly into a nanopore (e.g., as an epitope in a nanopore loop).

In some embodiments, a protein can be detected using a nanopore (e.g., a OmpG nanopore sensor). However, it should be appreciated that other biological substances, such as nucleic acids, protein complexes, bacteria, virus and cells might be detected using the same approach.

In some embodiments, methods are provided to optimize the target binding interface constituted by loops in a nanopore (e.g., OmpG). In some embodiments, a screening method is provided for the selection of the nanopore sensor with the required binding affinity to various target molecules. In some embodiments, OmpG is the nanopore and is derived from the outer member protein G in of a bacterium (e.g., a gram negative bacterium (e.g., *E. coli*)). In some embodiments, a library of nanopores (e.g., OmpG) is provided with the extracellular loops (e.g., 7 in total) of the nanopores substituted by randomized sequences. In some embodiments, these loops with randomized sequence may constitute high-affinity sites for target molecules to bind.

In some embodiments, when expressed in *E. coli*, OmpG is located in the outer membrane with its loops facing the environment. Thus, in some embodiments, target-specific clones can be selected by binding to an immobilized target molecule followed by washing to remove *E. coli* cells that don't interact with the target. (FIG. 4.) It should be appreciated that other bacterial systems and/or nanopores may be used. In some embodiments, a strong binder can be eluted, e.g., by changing the buffer conditions and culturing for amplification. In some embodiments, a plasmid from a stronger binder can be extracted from a culture to obtain a sequence of the OmpG protein. In some embodiments, this newly selected OmpG sensor can be massively produced by an established protocol. Thus, in some embodiments, biosensors can be selected for the detection of virtually any targets.

In some embodiments, OmpG homologs from other organisms can be used for sensing of large biological molecules. In addition, any pore-forming protein, e.g., porins from bacterial membrane and mitochondria membrane with flexible loops can be used to detect large molecules following the same methods disclosed herein. In some embodiments, synthetic molecules, e.g., synthetic peptides and polymers that form pores can be used for sensing in the same manner.

The antibody industry is continuously developing new and robust discovery platforms and novel antibody formats. In some embodiments, specific antibodies can be built on varied protein scaffolds after the introduction of an antigen binding site/interface. In some embodiments, these scaffold proteins differ greatly in their origin, function and structure. In some embodiments, some of their antigen binding sites do not share any sequence or structural homology with natural antibodies. In some embodiments, an antibody-like protein is provided that uses a nanopore (e.g., OmpG) as a scaffold. In some embodiments, the strategy integrates a high-affinity binding site into the extracellular loops of the nanopore (e.g., OmpG) (FIG. 1C). In some embodiments, this approach does not involve chemical modification to attach a ligand to the nanopore (e.g., OmpG).

In some embodiments, the nanopore has an amino acid sequence set forth as follows: >gi|159164722|pdb|2JQY|A Chain A, Outer Membrane Protein GEERNDWHFNIGAMYEIENVEGYGEDMDGLAEPSVYFNAAANGPWRIALAYYQEGPVD YSAGKRGTWFDRPELEVHYQFLENDDFSFGLTGGFRNYGYHYVDEPGKDTANMQ RW KIAPDWDVKLTDDLRFNGWLSMYKFANDLNTTGYADTRVETETGLQYTFNETVALRV NYYLERGFNMDDSRNNGEFSTQEIRAYLPLTLGNHSVTPYTRIGLDRWSNWDWQDDIE REGHDFNRVGLFYGYDFQNGLSVSLEYAFEWQDHDEGDSDKFHYAGVGVNYSF (SEQ ID NO: 5). In some embodiments, the nanopore has an amino acid sequence that is a mutated version of the amino acid sequence above. In some embodiments, the nanopore has an amino acid sequence set forth as follows: >Outer Membrane Protein—D224C GEERNDWHFNIGAMYEIENVEGYGEDMDGLAEPSVYFNAAANGPWRIALAYYQEGPVD YSAGKRGTWFDRPELEVHYQFLENDDFSFGLTGGFRNYG YHYVDEPGKDTANMQRW KIAPDWDVKLTDDLRF-NGWLSMYKFANDLNTTGYADTRVETETGLQYTFNETVALRV NYYLERGFNMDDSRNNGEFSTQEIRAYLPLTLGNHSVTPYTRIGLDRWSNWDWQCDIE REGHDFNRVGLFYGYDFQNGLSVSLEYAFEWQDHDEGDSDKFHYAGVGVNYSF (SEQ ID NO: 6).

In certain aspects of the invention, kits are provided, comprising a container housing a nanopore or composition. In some embodiments, individual components of a composition may be provided in one container. Alternatively, it may be desirable to provide the components of the composition separately in two or more containers, e.g., one container for a compound (e.g., a vasoactive agent), and at least another for a carrier. The kit may be packaged in a number of different configurations such as one or more containers in a single box or package. The different components can be combined, e.g., according to instructions provided with the kit. The components can be combined according to a method described herein, e.g., to prepare and administer a compound or composition. The kit can also include a delivery device.

The present invention is further illustrated by the following Examples, which in no way should be construed as further limiting.

EXAMPLES

Introduction

Nanopores are powerful single-molecule analytical tools that enable the study of fundamental problems in chemistry and biology, including protein folding, enzymatic activity and chemical reactions. Nanopores also are useful in applications such as DNA sequencing and biosensing. Molecular detection using a single nanopore works by observing modulations in ionic current flowing through the pore during an applied potential. Typically, binding (or translocation) of an analyte within (or through) the pore's lumen partially blocks the flow of current and provides information about a molecule's size, concentration and affinity. Nanopores based on protein toxins, such α-hemolysin (αHL), may be used to detect metal ions, organic molecules, and oligonucleotides.

In some cases, although αHL works well for small analyte detection, molecules larger than 27 Å in diameter cannot fit in the pore's lumen. Strategies may be utilized to transmit a binding signal from solution to the pore interior to facilitate protein detection. For example, binding of a kinase may be performed using an αHL pore modified with an inhibitor peptide attached to its trans side. Detection of streptavidin may be performed by tethering biotin via a long polyethylene glycol (PEG) polymer to αHL.

As an alternative strategy, protein detection may be also be accomplished using a larger nanopore. For example, the bacterial toxin ClyA, with a 70 Å diameter, may be modified at one end with an aptamer specific to thrombin. Synthetic nanopores larger than 60 Å diameter may be used to identify proteins either during translocation or through capture by specific receptors immobilized on the wall of the pore.

In contrast with other multimeric proteinaceous nanopores such as αHL and ClyA, outer membrane protein G (OmpG) from *Escherichia coli* (*E. coli*) is monomeric. Thus, complex and asymmetric alterations by chemical or genetic modifications may be performed, making OmpG an advantageous nanopore platform for developing nanopore-based sensing technology. OmpG is composed of 14 β-strands connected by seven flexible loops on the extracellular side and seven short turns on the periplasmic side (FIG. 1A). The extracellular opening is 8 Å in diameter and the periplasmic side is 14 Å. Wild-type OmpG spontaneously gates during an applied potential as revealed by planar bilayer studies.

Figure 1B:
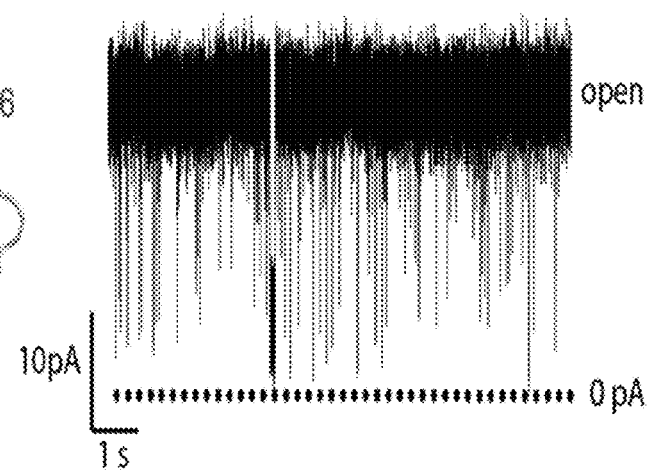
Figure 1C:
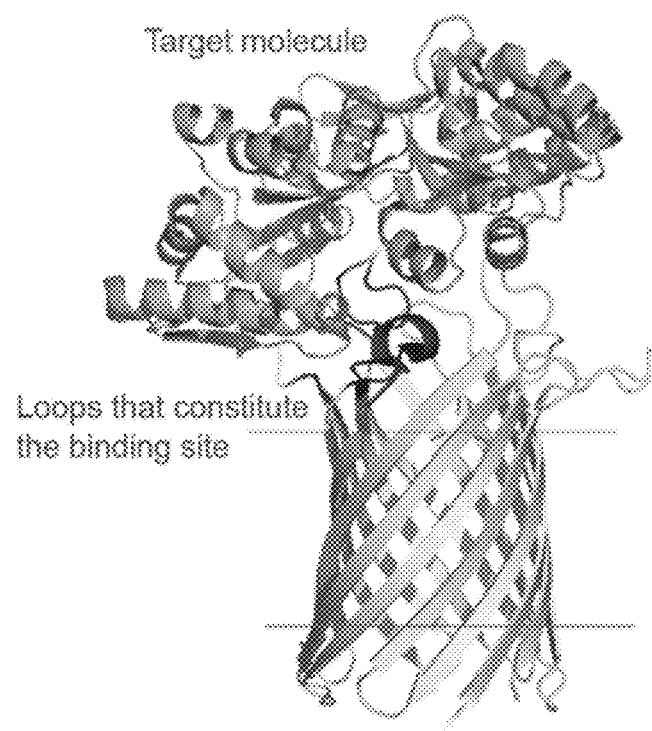
FIG. 1C shows integration of a binding site to a loop region of OmpG.

Pore gating is attributed to loop 6 which flops in and out of the pore, intermittently blocking the current (FIGS. 1A, 1B). To reduce gating, a disulfide bond or lipid anchor was introduced into OmpG's structure which effectively pinned the flexible loop 6 in place. The resulting quiet OmpG was used to sense ADP in the presence of a cyclodextrin adapter.

In some cases, a rigid and stable structure is may be advantageous for protein pores for sensing. Examples of protein pores for certain sensing applications include αHL, MspA, ClyA and phi29 DNA packaging motor all of which are homo-oligomers that possess a rigid structure. Two monomeric outer membrane porins, OmpG and FhuA with flexible loops have been used for sensing purposes. However, in such cases, the flexible loops were either fixed or removed to stabilize a single open conformation by protein engineering. In contrast, in this example, loop dynamics were directly exploited instead of pore blockage to detect protein interactions. The results demonstrate that the flexibility of OmpG's structure represents a unique feature, which can be used for resolving subtle differences between the surface properties of highly homologous protein analytes.

In this example, a biological nanopore OmpG is provided that can be used to detect large proteins without the need for an analyte to enter the pore lumen. The OmpG sensor was constructed by tethering a ligand to a dynamic loop of OmpG. Binding of the target protein streptavidin to its specific ligand biotin slowed down the dynamic movement of the loop, thereby significantly altered the ionic current gating signal. This principle of detection is applicable to other biological samples such as virus particle or bacterial. The monomeric feature of OmpG makes it particularly amendable to incorporate high-affinity peptide directly to its loops for detection of other proteins.

Materials and Methods:
Materials:

The DNA oligonucleotides and all chemicals were purchased from Fisher Scientific unless stated otherwise. Streptavidin (Z7041) was purchased from Promega. The biotin-maleimide reagents, Maleimide-PEG$_2$-Biotin and Maleimide-PEG$_{11}$-Biotin were purchased from Piercenet (Thermo Scientific). Mouse anti-biotin monoclonal antibody (MS-1048-P1) was purchased from Thermo Scientific. Goat anti-biotin polyclonal antibody (B3640) was from Sigma Aldrich. LB media was purchased from Boston BioProducts.

Diphytanoylphosphatidylcholine (DPhPC) were from Avanti polar lipids. Octyl-glucoside (OG) was purchased from GoldBio Technology.

Construction of OmpG D224C Mutant:

Single cysteine was introduced to replace the aspartic acid 224 by mutagenesis PCR based on the plasmid pT7-OmpG wt. The primers for D224C were 5'-GGGACTGGCAGT-GTGATATTGAACGTGAAG (forward, SEQ ID NO: 1) and 5'-GTTCAATATCACACTGCCAGTCCCAGTTAC (reverse, SEQ ID NO: 2). These two primers were used in a pair with the primer SC47: 5'-CAG AAG TGG TCC TGC AAC TTT ATC (reverse, SEQ ID NO: 3) and SC46: 5'-ATA AAG TTG CAG GAC CAC TTC TG (forward, SEQ ID NO: 4) which annealed to the middle of the plasmid. The two PCR products were mixed in a 1:1 molar ratio and subjected to DpnI digestion for three hours to degrade the parental plasmid. E. coli DH5α cells were then co-transformed with the PCR mixture and colonies containing the desired mutant construct pT7-OmpG D224C was identified by DNA sequencing. All primers were obtained from Fisher Scientific.

Accordingly, the sequence of the loop6 in wild type protein is: 218-SNWDWQD(224)DIERE (SEQ ID NO: 7); whereas the sequence of loop6 in the mutated version is: SNWDWQC(224)DIERE (SEQ ID NO: 8). In some embodiments, the mutated version is: SNWC(221)WQD-DIERE (SEQ ID NO: 9).

Cloning, Expression and Purification of OmpG D224C:

Single cysteine was introduced to replace aspartic acid 224 by mutagenesis PCR based on the plasmid pT7-OmpG wt (Supplementary information). The OmpG D224C was prepared as follows. The pT7-OmpG D224C was transformed into the BL21(pLys) E. coli cells and cells were grown in LB medium at 37° C. until the OD600 reached 0.5. IPTG (0.5 mM) was added to the culture to induce the protein expression. Cells were harvested 3 hours after induction and lysed in lysis buffer (50 mM Tris·HCl, pH 8.0, 150 mM NaCl, 200 µg/ml lysozyme, 1 mM EDTA, 1 mM PMSF). Cells were sonicated on ice to break the bacterial membranes. DNAse I (5 ul, 2,000 U/µl) and 2 mM MgCl$_2$ were then added to the mixture to decrease the viscosity. The lysate was centrifuged at 13,000 rpm for 30 min. The pellet was washed once with 30 ml 50 mM Tris·HCl, pH8.0, 1.5 M Urea. Then the OmpG-containing inclusion body was dissolved in 50 ml 50 mM Tris, pH 8.0, 3 mM Tris(2-carboxyethyl)phosphine (TCEP), 8 M Urea and passed through a 0.22 µm filter before FPLC purification. All OmpG proteins were purified using a Q-ionic exchange column (GE Healthcare).

Biotinylation and Refolding of OmpG Proteins:

The purified OmpG D224C was incubated with 10 mM freshly prepared DL-dithiothreitol (DTT) for 30 min on ice to reduce the thiols. The DTT was then removed using a desalting column equilibrated with buffer 50 mM HEPES, pH7.0, 150 mM NaCl, 8M Urea. To label the OmpG D224C with biotin, the protein was incubated with maleimide-PEG-biotin in a molar ratio 1:20 (protein to biotin) at room temperature (~23° C.) for 2 hours and then at 4° C. overnight. DTT (10 mM) was added to quench the reaction. The reaction mixture was passed through the desalting column once again to remove the unreacted chemicals. The biotin labelled OmpG was then refolded in refolding buffer (50 mM Tris·HCl, pH 9.0, 3.25% OG, 3.0 M Urea) at 37° C. for 3 days. The biotinylation and refolding efficiency was determined by SDS-PAGE (FIG. 9).

Figure 4A:
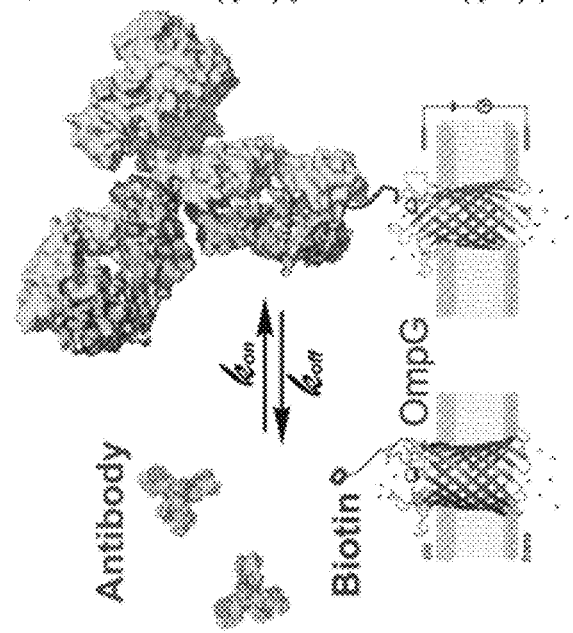
FIGS. 4A-4E depicts the detection of monoclonal anti-biotin antibody by OmpG-PEG$_2$-biotin pore.

Single Channel Recording of OmpG Proteins:

Single channel recording of OmpG was performed. Briefly, assays were performed in an apparatus containing two chambers separated by a 25 µm thick Teflon film. An aperture of approximately 100 µm diameter had been made near the center of the film with an electric spark. The aperture was pretreated with a hexadecane/pentane (1:10 v/v) solution before each chamber was filled with buffers as indicated specifically. An Ag/AgCl electrode was immersed in each chamber with the cis chamber grounded. 1,2-Diphytanoyl-sn-glycerol-3-phosphocholine (Avanti Polar Lipids, USA) dissolved in pentane (10% w/v) was deposited on the surface of the buffer in both chambers and monolayers formed after the pentane evaporated. The lipid bilayer was formed by raising the liquid level up and down across the aperture. OmpG proteins (~1 nM, final concentration) were added to the cis chamber and +200 mV was applied to facilitate OmpG insertion. After a single OmpG pore inserted, the applied voltage was lowered to 50 mV for recording. OmpG proteins inserted in the planar lipid bilayer bi-directionally with its extracellular loops located at either cis or trans side. After 10 mins recording, the orientation of the OmpG pore in the lipid bilayer was determined by analyzing the asymmetrical gating pattern at positive and negative potentials. Streptavidin or antibodies were added to the cis or trans chamber depending on the pore orientation and the solution was stirred for 10 s. Positive potential was defined such that the potential of the chamber in which the extracellular loops were exposed to is positive (e.g., as shown in FIG. 4A). For example, a positive potential indicates a higher potential in the trans chamber. Current was amplified with an Axopatch 200B integrating patch clamp amplifier (Axon Instruments, Foster City, Calif.). Signals were filtered with a Bessel filter at 2 kHz (unless otherwise stated) and then acquired by a computer (sampling at 50 μs) after digitization with a Digidata 1320A/D board (Axon Instruments).

Engineered OmpG as a Biosensor for Detecting Ligand-target Interactions:

OmpG has been engineered to detect nucleotides. The flexible loop 6 was stabilized to an open conformation to reduce the gating. The resulted quite OmpG was used to sense ADP after equipped with a cyclodextrin adapter. To detect proteins, an OmpG nanopore with a ligand tethered to a single cysteine on loop 6 in order to "fish" for target protein was constructed. It was hypothesized that target binding would alter the flexibility of loop 6 and therefore alter the gating pattern to generate a recognizable signal to indicate detection. To validate the concept of the OmpG sensor, biotin and streptavidin were chosen as the model ligand and target protein because of its very low dissociation constant.

Figure 2A:
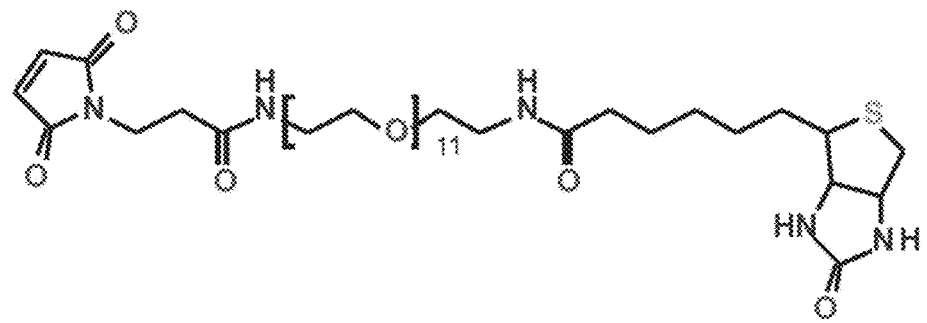
Figure 2A:
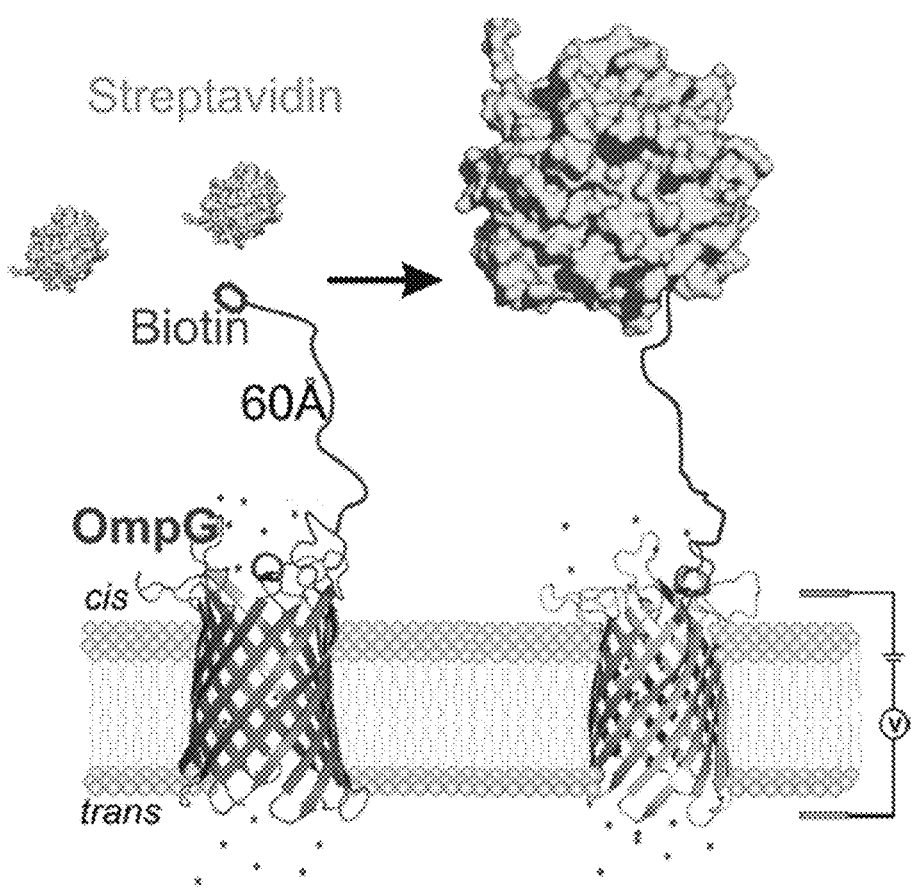
Figure 13A:
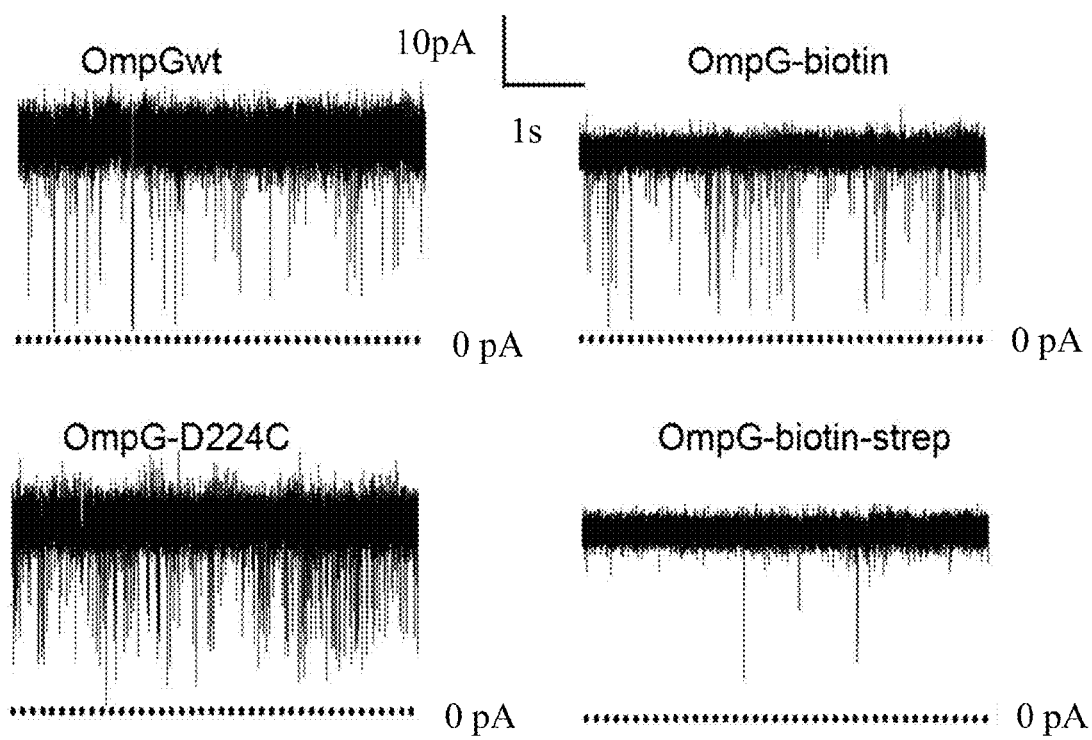

A single cysteine was introduced to replace an aspartic acid 224 on loop 6 by site-directed mutagenesis (FIG. 1A). The cysteine was labeled with PEG-biotin which extends out from OmpG in aqueous solution by ~29 Å (FIG. 2). The gating pattern of biotinylated OmpG was examined by single channel recording and its behavior was indistinguishable from that of the wild type (FIG. 13A). Thus, it was surmised that adding an extra ~500 Da mass to Loop 6 did not significantly alter its flexibility.

Figure 2C:
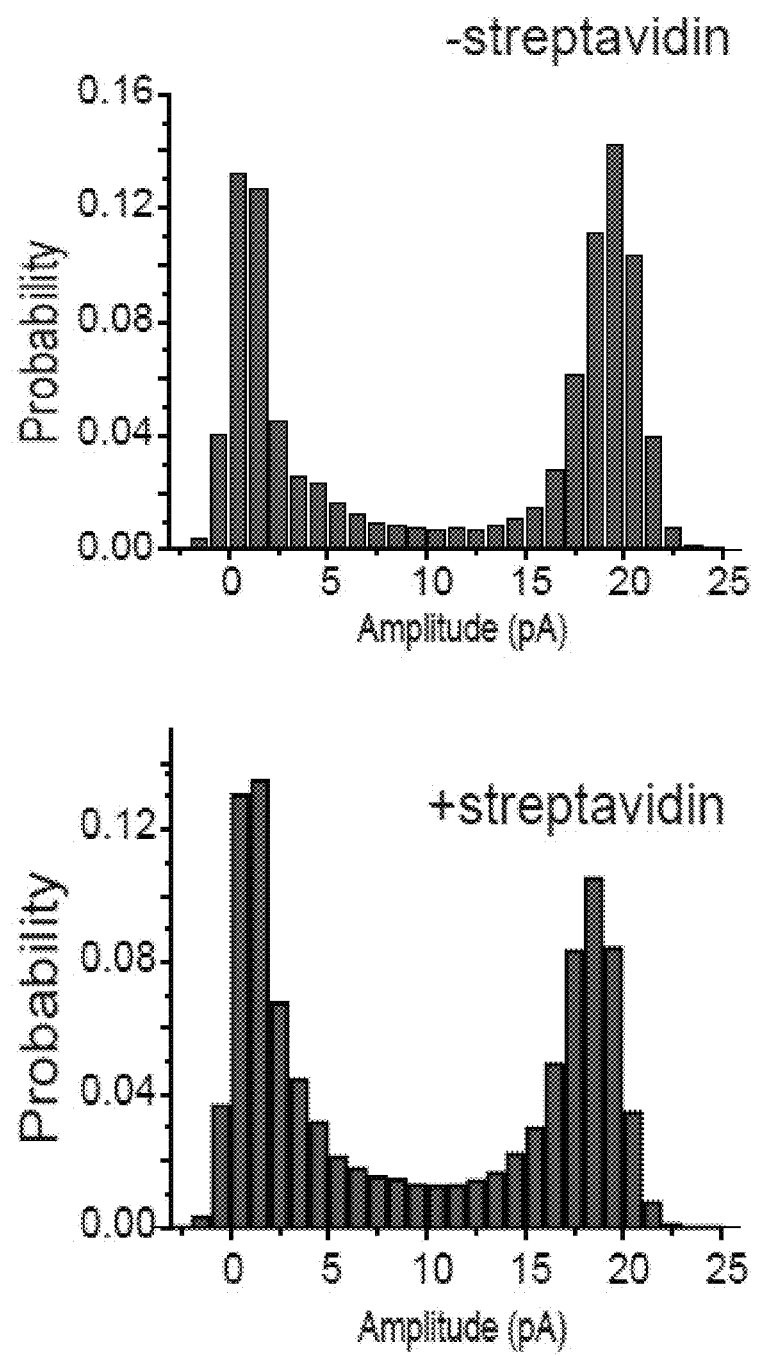
Figure 13D:
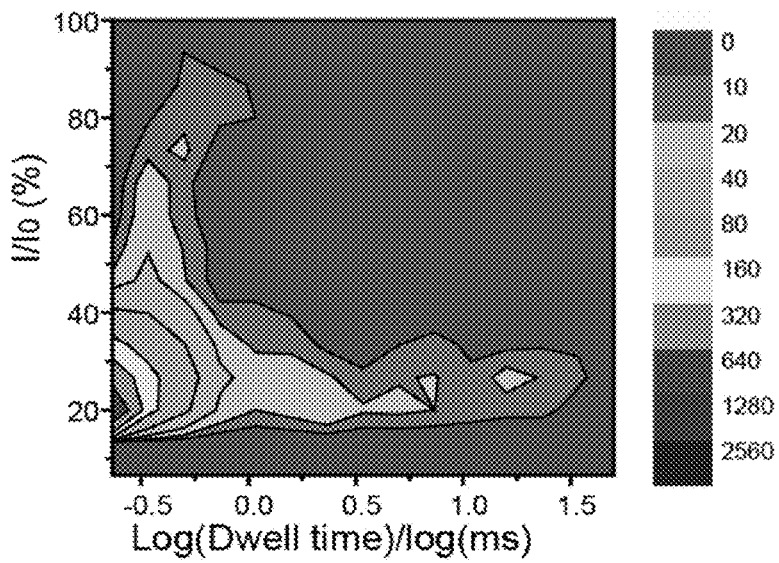
Figure 14:
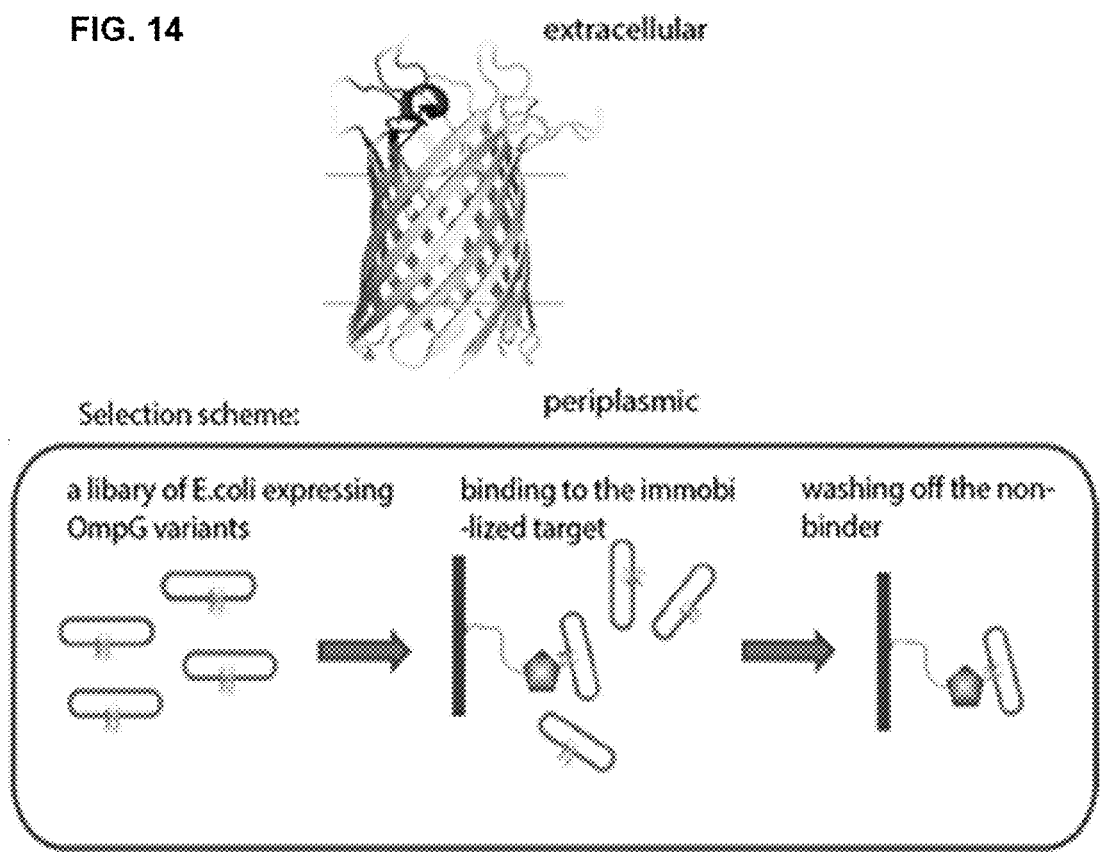
FIG. 14 depicts an OmpG sensor library.

Since OmpG can incorporate into a planar bilayer in one of two possible orientations, it was necessary to determine which side of the membrane the biotin-tethered end of OmpG was located. Previous studies showed that wild type OmpG inserts into the planar bilayer bidirectionally with either the extracellular loops or the periplasmic turns penetrating through the bilayer during the insertion. The orientation of a single OmpG channel in the planar lipid bilayer was determined by its unique asymmetric gating pattern and unitary current conductance. These characteristics were used to determine that OmpG-biotin preferentially inserted into the lipid bilayer by its short periplasmic turns, thus leaving the extracellular loops exposed to the cis chamber (FIG. 2B). Thus, streptavindin (3 nM) was added to the cis recording chamber which was then stirred for 10 S. Pore gating was monitored at +50 mV and when streptavidin bound to the biotinylated OmpG, the gating was greatly reduced (FIG. 13). It was typically observed in less than ~1 mM after the stirring (FIG. 13B). The change in gating can be categorized in two distinct ways. Namely, both the frequency and amplitude of gating events were reduced (FIGS. 2C and 2D, respectively). To quantitatively evaluate the effect of the binding on gating, two parameters were introduced: (i) the gating frequency (f, events/s), defined as the total number of gating events divided by the recording time; and (ii) the gating probability (Pgating), defined as the total time for which a pore is in the closed or partially closed state divided by the total recording time (total open and closed time). The former is a direct measure of the gating activity of the pore and the latter describes the equilibrium between the closed and open states. The gating properties derived from the traces at +50 mV of each OmpG variant are summarized (FIG. 2C). The biotinylated OmpG behavior is indistinguishable from that of the wild type protein. After streptavidin binding, the Pgating decreased drastically from 0.068±0.060 to 0.013±0.014, by 5 fold. The gating event frequency was reduced from 4.3±3.2/s to 1.3±1.5/s. Thus, binding of the streptavidin to the OmpG-biotin nanopore can be detected via changes in gating behavior. As a control, streptavidin was added to OmpG D224C channel and no change was observed to any of the single channel (10 pores) tested.

To gain insight into how the attachment of a large protein to loop 6 affects its movement (gating), the electrical recording traces were examined in further detail. The 2-dimentional (2D) event distribution plot shows that that a large proportion of events with long dwell time (>1 ms) and large amplitude (>40%) disappeared after streptavidin binding. To induce such a large current block, one third of β-strand 12 that connects with loop 6 unfolds and extends into loop 6. The elongated loop is then capable of bend over to the opposite site of lumen and blocks mostly the entrance. These results indicate that although the dynamic movement of loop 6 generally slows down after being tethered to a 13 kD protein, its movement of bending to the opposite of the lumen was affected. According to the crystal structure, the D224 traverses approximately 7.5 Å between the open and closed states. However, based on NMR, loop dynamics of OmpG shows this residue may migrate as far as ~40 Å between the fully open and closed conformers. The results indicate that such a large movement was affected by streptavidin binding. Two factors may contribute to this effect in some cases: i) the thermal energy of loop 6 may be insufficient to move a protein of 13 kDa such a distance. ii) Attaching streptavidin may introduce steric hindrance for loop 6 that prevents it from fully bending to the opposite wall.

In summary, binding of the target protein to OmpG-biotin nanopore reduced the movement of the loop 6 and altered the gating pattern. This is the first time that protein detection has been demonstrated for a monomeric protein nanopore. The principle of monomeric (e.g., OmpG) nanopore sensing involves detecting modulation of loop dynamics upon target protein binding rather than occupation of the pore lumen as in the prior nanopore sensing. This approach is applicable to a broader spectrum of analytes, such as proteins, virus, or bacteria without the need to use a far larger nanopore. The monomeric feature of OmpG makes it particularly interesting to incorporate high-affinity peptide into its loop for direct detection of proteins.

Detection of Streptavidin by OmpG-PEG$_{11}$-biotin Pore.

To detect proteins, an OmpG nanopore with a ligand tethered to loop 6 to "fish" for target proteins was designed. It was hypothesized that target binding would alter the flexibility of loop 6 and therefore alter the gating pattern as a recognizable signal to indicate detection. To validate the concept of the OmpG sensor, biotin and streptavidin were first chosen as the model ligand and target protein because of its very low dissociation constant of ~$10^{-15}$M. A single cysteine mutation was introduced to the D224 residue of OmpG by site-directed mutagenesis (FIG. 1). The OmpG D224C was expressed in *E. coli* as inclusion bodies and purified by ion-exchange chromatography. Purified OmpG D224C proteins were labeled with maleimide-(PEG)$_{11}$-biotin and the resulting OmpG-PEG$_{11}$-biotin construct was refolded to its native structure (FIG. 9). The biotin group extends out from the OmpG pore by approximately 60 Å to facilitate the capture of the analyte proteins (FIG. 2A). Single-channel recording of OmpG-D224C and OmpG-PEG$_{11}$-biotin revealed that neither the mutation nor the tethered biotin group induced a measurable change in the unitary conductance or gating pattern of OmpG when compared to the wild type protein. In the presence of 3 nM streptavidin, a marked increase in gating frequency from 111±30 s$^{-1}$ to 199±27 s$^{-1}$ (n=3) was observed for OmpG-PEG$_{11}$-biotin pore at pH 6.0 (FIG. 2B).

Figure 10:
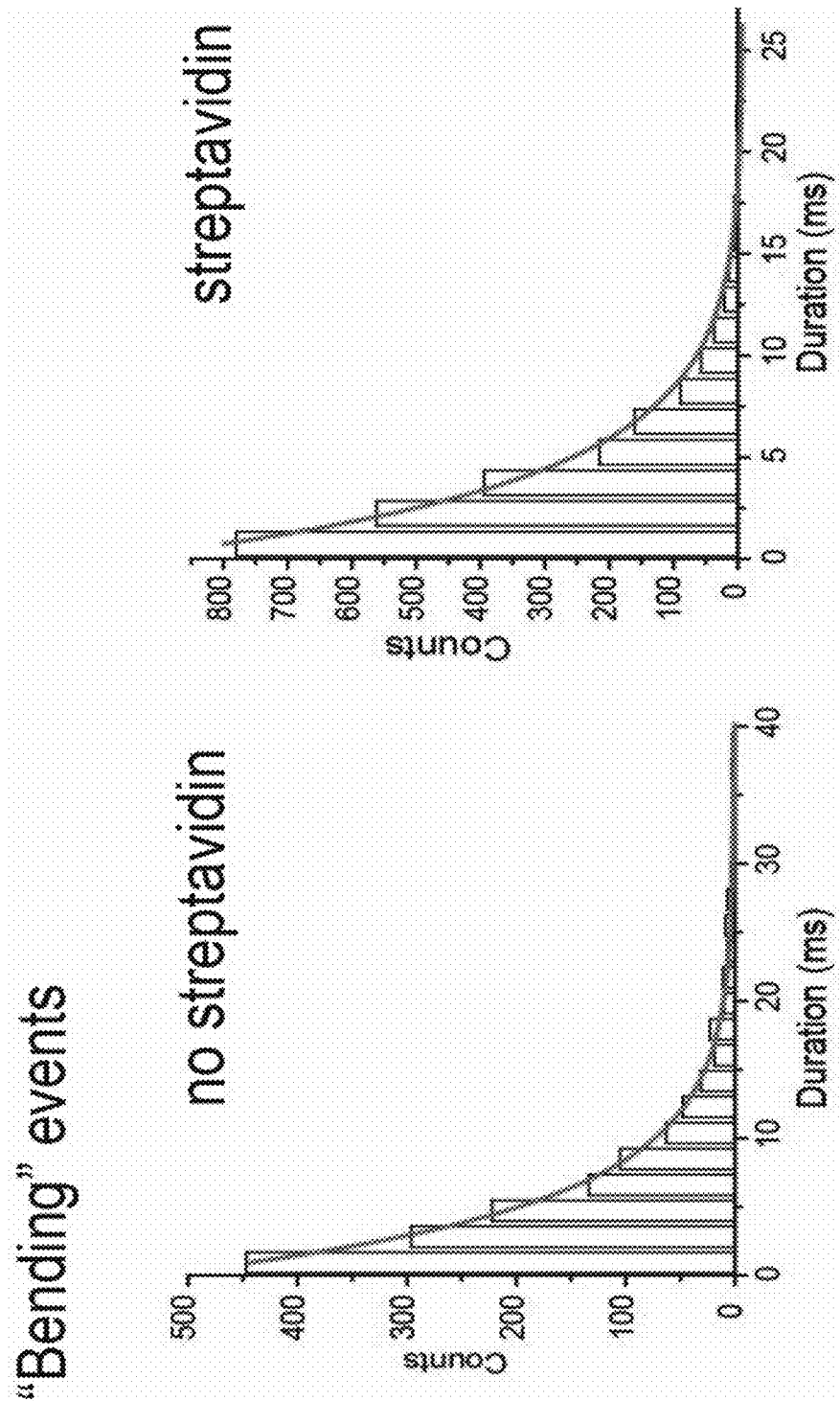
FIG. 10 shows the effect of streptavidin binding on the bending events. A histogram of the duration time ($\tau_{off}$) of the gating events before and after streptavidin binding to OmpG-PEG$_{11}$-biotin is shown. Data were fitted with single exponential function yielding an average $\tau_{off}$ of 5.0 s and 3.9 s.

All the gating events according to their gating amplitude and duration were plotted in a two-dimensional (2D) event distribution plot (FIG. 2D). From the 2D plot analysis, two populations of events were observed. One only partially blocks the pore with amplitudes smaller than 7.5 pA and dwell time shorter than 0.4 ms; the other population almost fully blocks the pore with amplitudes larger than 10 pA and dwell time longer than 1 ms. From known structures of OmpG, it is expected that loop 6 cannot fully block the pore on its own as it cannot occupy sufficient space within the lumen. For complete blockage, it is expected that as much as one third of strand 12 may also unfold so that loop 6 is long enough to completely occlude the opening. The terms "flickering" and "bending" were given to describe partial vs complete blockades, respectively. This distinction is relevant when evaluating the behavior observed in the 2D plots. For example, flickering events seem relatively constant in the presence or absence of target, while the bending events shorten considerably when the target binds (FIG. 2C). By contrast, the average dwell time of the bending events decreased from 5.1±0.14 ms to 3.8±0.15 ms (n=3) (FIG. 10) when streptavidin was bound. In particular, those bending events of especially long duration (>10 ms), indicated with red asterisks, were eliminated during the streptavidin-bound state (FIGS. 2B, 2D). In some embodiments, the bending events may be shortened by bound streptavidin by destabilizing the closed state. However, due to the increased gating frequency, the open probability of the OmpG pore actually reduced slightly from 0.58±0.09 to 0.51±0.10 (n=3) upon streptavidin binding as revealed by the increase of the closed state peak (FIG. 2C). Overall, target binding induces a clear change in the gating properties of OmpG.

Shorting the Ligand Linker to Strengthen Signal.

The binding between the OmpG-PEG$_{11}$-biotin and streptavidin produced a relatively small effect on the gating. In some embodiments, length of the polyethylene linker may be adjusted to control dynamic movement of loop 6. Therefore, in one embodiment, the length of the PEG linker was shortened to just two units, creating the OmpG-PEG$_2$-biotin construct where the biotin extends ~29 Å into solution (FIG. 3A). The shortened linker did not affect the gating pattern when compared to OmpG D224C (data not shown). By shortening the linker, the effect of streptavidin binding was much more pronounced, permanently reducing the frequency and amplitude of gating events (FIGS. 3B, 3C). Quantitative analysis of three OmpG-PEG$_2$-biotin pores showed that the gating event frequency was reduced by more than 6 folds from 104±6 s$^{-1}$ to 16±2 (n=3). Comparison of the two-dimensional plots of all events reveals that the occurrence of bending events with long duration time (>1 ms) and high intensity (>10 pA) were mostly eliminated due to streptavidin binding (FIG. 3D). Gating events of transient duration time (<100 μs) and low intensity (<10 pA) still persist albeit with greatly reduced frequency. The data indicate that streptavidin bound to the PEG$_2$ linker can strongly restrict bending but not the flickering of loop 6. As a control, streptavidin was added to OmpG D224C pores and no change was observed (10 pores tested). Adding excess BSA (1 μM) to the OmpG-PEG$_2$-biotin pore also did not show any effect (data not shown). These observations confirmed that the alteration of the gating pattern is caused by the specific interaction between the streptavidin and the tethered biotin ligand. In summary, binding of streptavidin to the OmpG-PEG$_2$-biotin nanopore can be detected via changes in gating behavior.

Detection of Reversible Antibody Binding.

Figure 4B:
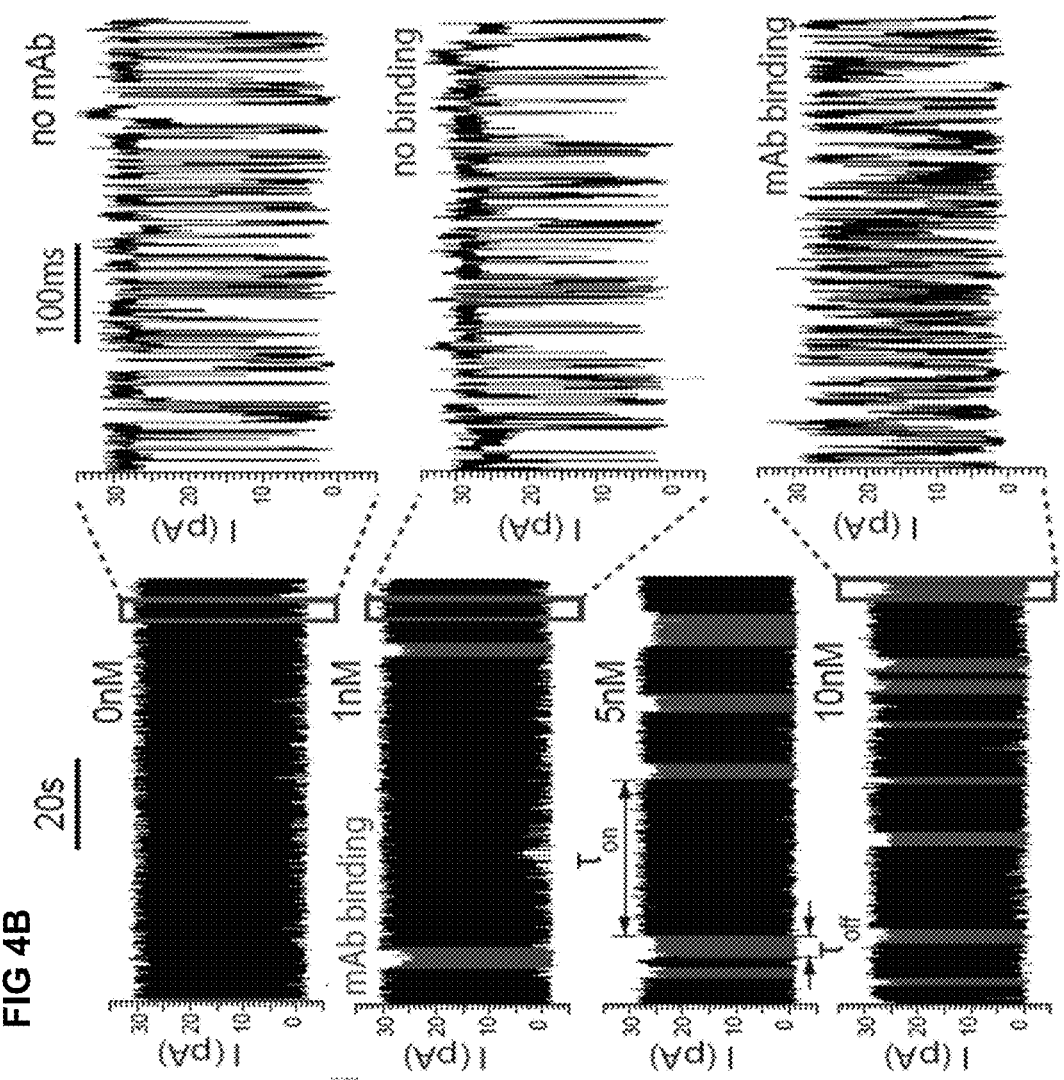
Figure 4C:
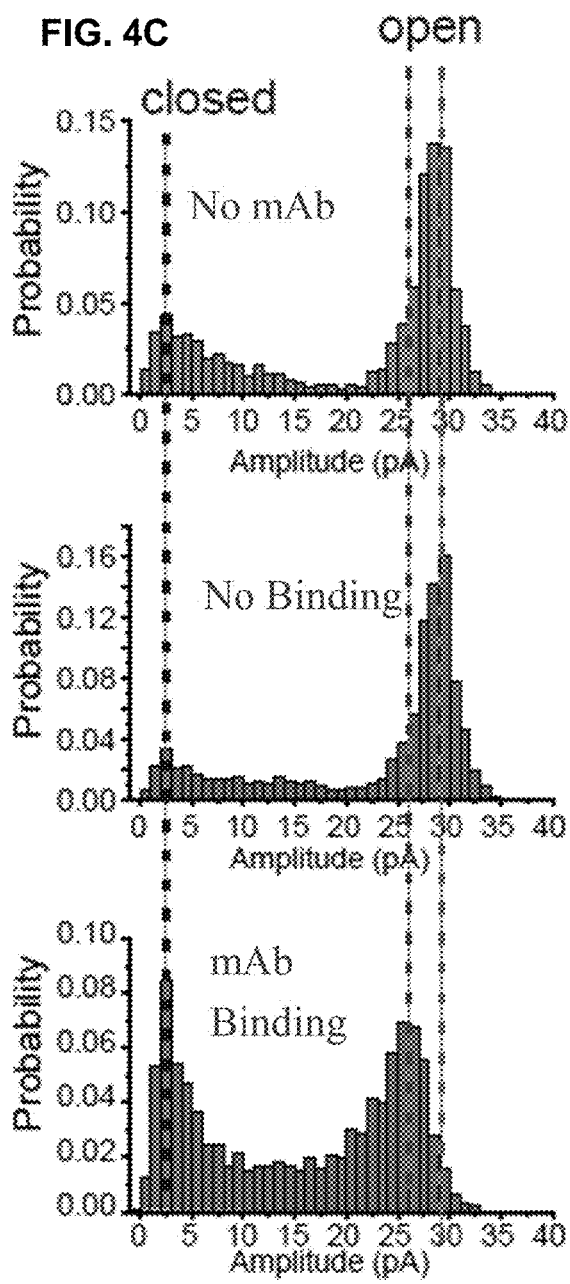

The biotin-streptavidin interaction is effectively irreversible, thus only one binding event can be detected with the nanopore sensor. Here, proteins with weaker dissociation constants were introduced to look at reversible interactions. Mouse monoclonal anti-biotin antibodies (mAb) were added to a recording chamber with a single OmpG-PEG$_2$-biotin (FIG. 4A). The electrical trace showed that the presence of biotin-antibody induced a dose-dependent gating pattern that was distinct from the streptavidin bound state (FIG. 4B). During antibody binding, the pore shifted to more closed conformation as revealed by the larger closed state peak in the all current histograms (FIGS. 4B, 4C). Indeed the calculated open probability was reduced from 0.73±0.04 at the no binding to 0.52±0.04 at the bound state (n=6). In addition, although the current fluctuates between open and closed states during both the antibody-free and antibody-bound states, the current of the pore in the fully open conformation was slightly reduced by 3.5±0.86 pA (13.6±3.8%, n=6) during the antibody bound state compared to the unbound state (FIG. 4C). This effect was not observed during the experiments using streptavidin and might suggest that the antibody is in closer proximity to the pore opening when bound. As a control, mouse anti-his tag monoclonal antibodies (20 nM) were not detected by current recording. Thus, it is believed that these gating events resulted from the anti-biotin antibody binding to the tethered biotin.

Figure 4D:
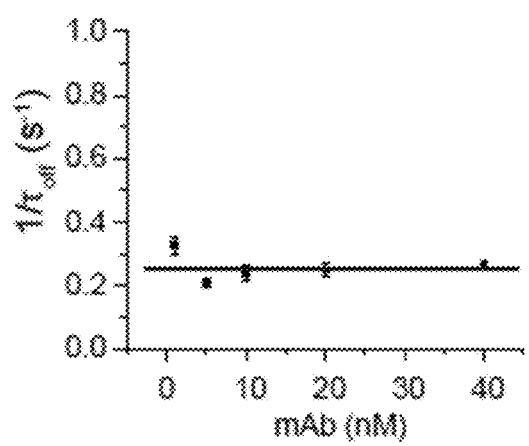
Figure 4E:
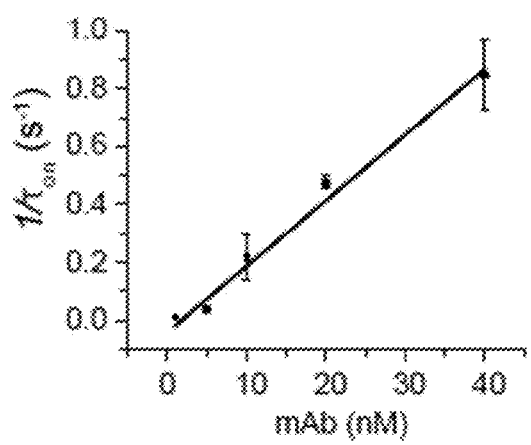

Next, the dwell time ($\tau_{off}$) and inter-event intervals ($\tau_{on}$) of mAb binding was calculated. The average dissociation rate constant ($k_{off}=1/\tau_{off}$) of the mAb binding events was 0.25±0.04 s$^{-1}$ (n=4) which was independent of the antibody concentration (FIG. 4D). The observed association constant ($k_{on}'=1/\tau_{on}$) increased linearly with the increasing concentration of antibody (FIG. 4E). The association rate constant $k_{on}$ of antibody binding was 2.30±0.43×10$^7$M$^{-1}$·s$^{-1}$ (n=4). The affinity binding constant ($K_d$) of the mouse monoclonal antibody to biotin was 1.12×10$^{-8}$±0.28 M$^{-1}$ (n=4). At the lowest mAb concentration tested (1 nM), the mean inter-event interval was 74.5±31 s meaning the OmpG-PEG$_2$-biotin sensor can detect 1 nM anti-biotin mAb within tens of min.

Influence of Voltage on the mAb Binding.

Figure 5A:
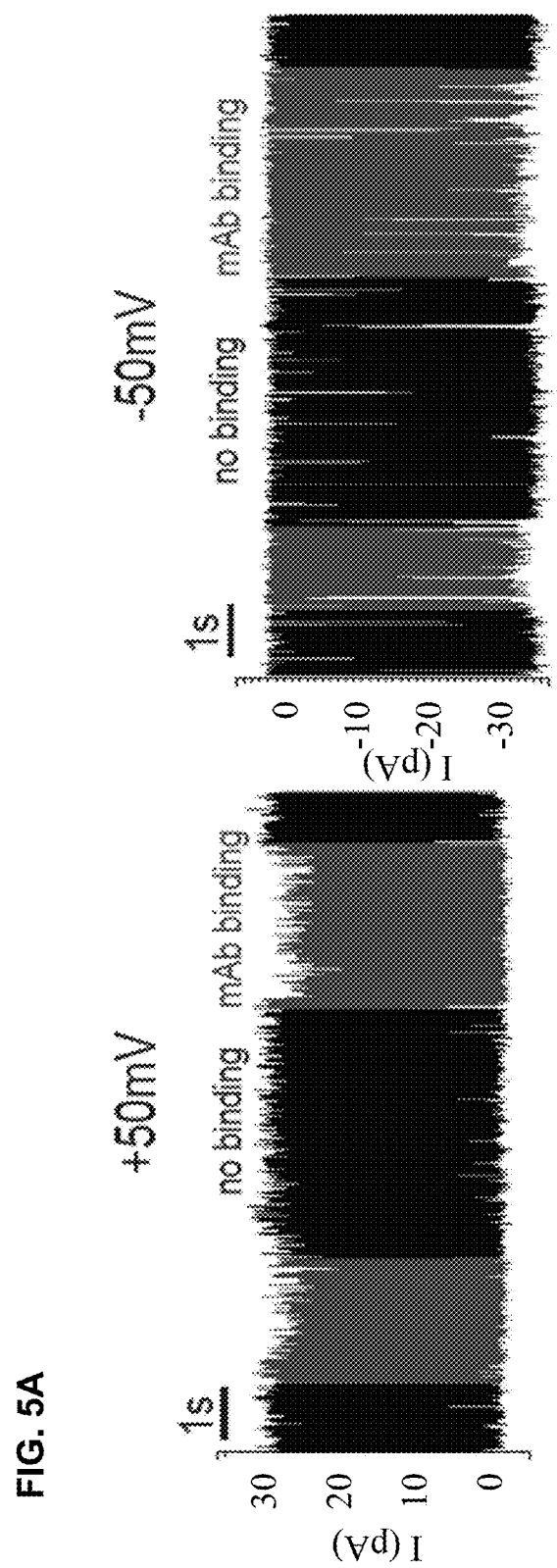
FIGS. 5A-5D show the effect of voltage on the mAb binding.
Figure 5B:
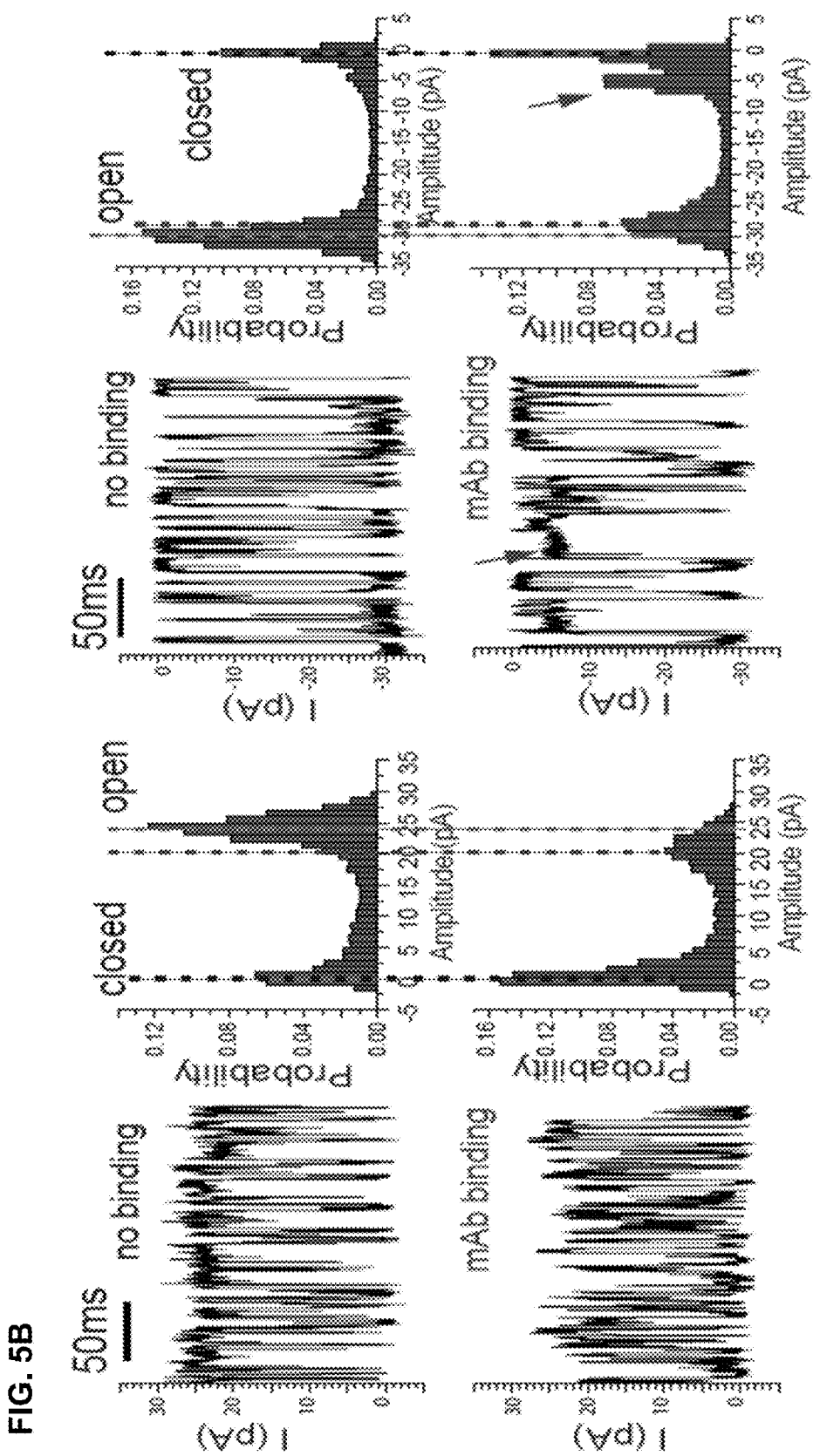

OmpG exhibits asymmetrical gating pattern at positive and negative voltages. Therefore, it was assess whether the polarity of the voltage similarly affects the dynamic motion of loop 6 during the mAb bound state. FIG. 5A shows that mAb binds to OmpG-PEG$_2$-biotin at both +50 mV and −50 mV. The open probability of the mAb bound state at +50 mV and −50 mV is 0.52±0.04 (n=6) and 0.40±0.09 (n=6) respectively, in comparison to 0.73±0.04 (n=6) and 0.71±0.01 (n=3) of the non-binding state. Thus in the mAb bound state, the pore switched to a slightly more closed state at the negative potential (FIG. 5B). OmpG pore also showed a decreased current by 1.2±0.4 pA (n=3) at its fully open state at −50 mV. This decrease is ~5.4% of the current of a no binding state in comparison to the 13.6% decrease at the positive potential. Moreover it had a partial closure state with 6 pA of residual current as indicated by the red arrow in the recording trace and all current histograms (FIG. 5B). This result shows that the loop gating during the mAb bound state is still strongly influenced by the polarity of the applied potential. This is a useful feature that can be used for sensing and shape produce unique signals, it is hypothesized that the OmpG sensor recognizes unique targets based on other factors such as charge, hydrophobicity or perhaps post-translational modification of the surface.

TABLE 1

Fingerprint of each type of gating events

|  | Open probability | Event frequency (s$^{-1}$) | Inter-event duration (s) | Gating duration (s) | Relative conductance of open state (%) |
|---|---|---|---|---|---|
| No binding | 0.73 ± 0.04* | 97 ± 3.6 | 8.68 ± 2.14 | 2.93 ± 0.52 | 100 |
| mAb | 0.52 ± 0.04 | 201 ± 103 | 3.67 ± 1.57 | 4.20 ± 1.90 | 86.4 ± 1.3 |
| pAb.1 | 0.99 ± 0.01 | 7 ± 1 | n/a | n/a | 52.3 ± 4.7 |
| pAb.2 | 0.94 ± 0.02 | 57.5 ± 2 | 12.2 ± 1.3 | 1.09 ± 0.21 | 106.5 ± 6.5 |

*Values were calculated from at least three independent experiments. The errors indicate the standard deviation.

because the asymmetric response of OmpG to target protein binding adds one more parameter for specific analyte protein recognition.

Figure 5C:
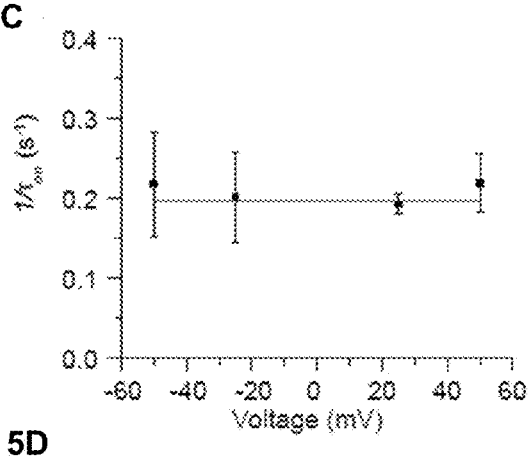
Figure 5D:
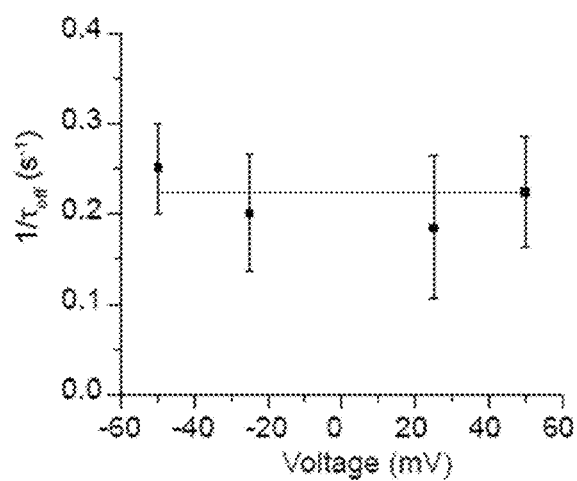

Since voltage may alter analyte binding kinetics, single channel recording was performed at applied voltages ranging from −50 mV to +50 mV in the presence of mouse mAbs. The voltage-dependent gating of OmpG prevented us from testing higher potentials as OmpG tends to close completely at ±75 mV. Neither $\tau_{on}$ nor $\tau_{off}$ exhibited a strong dependence on voltages (FIGS. 5C, 5D). Thus, it was concluded that the applied potential does not affect mAb binding to biotin. The independence of binding from voltage is advantageous since proteins can be analyzed regardless of the applied potential.

Simultaneous Detection of Mouse mAb and Goat Polyclonal Biotin Antibody.

Figure 6A:
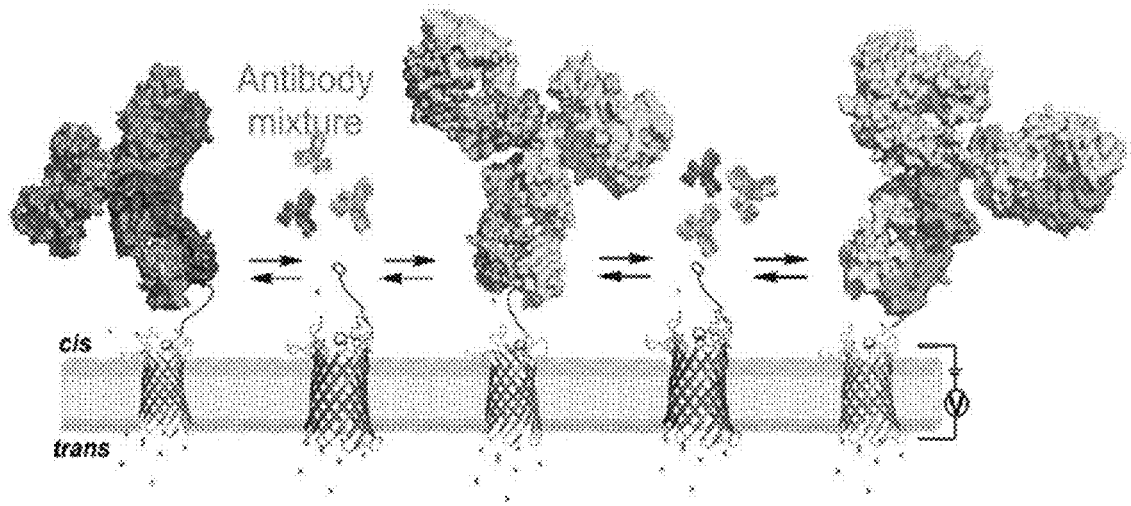
Figure 6C:
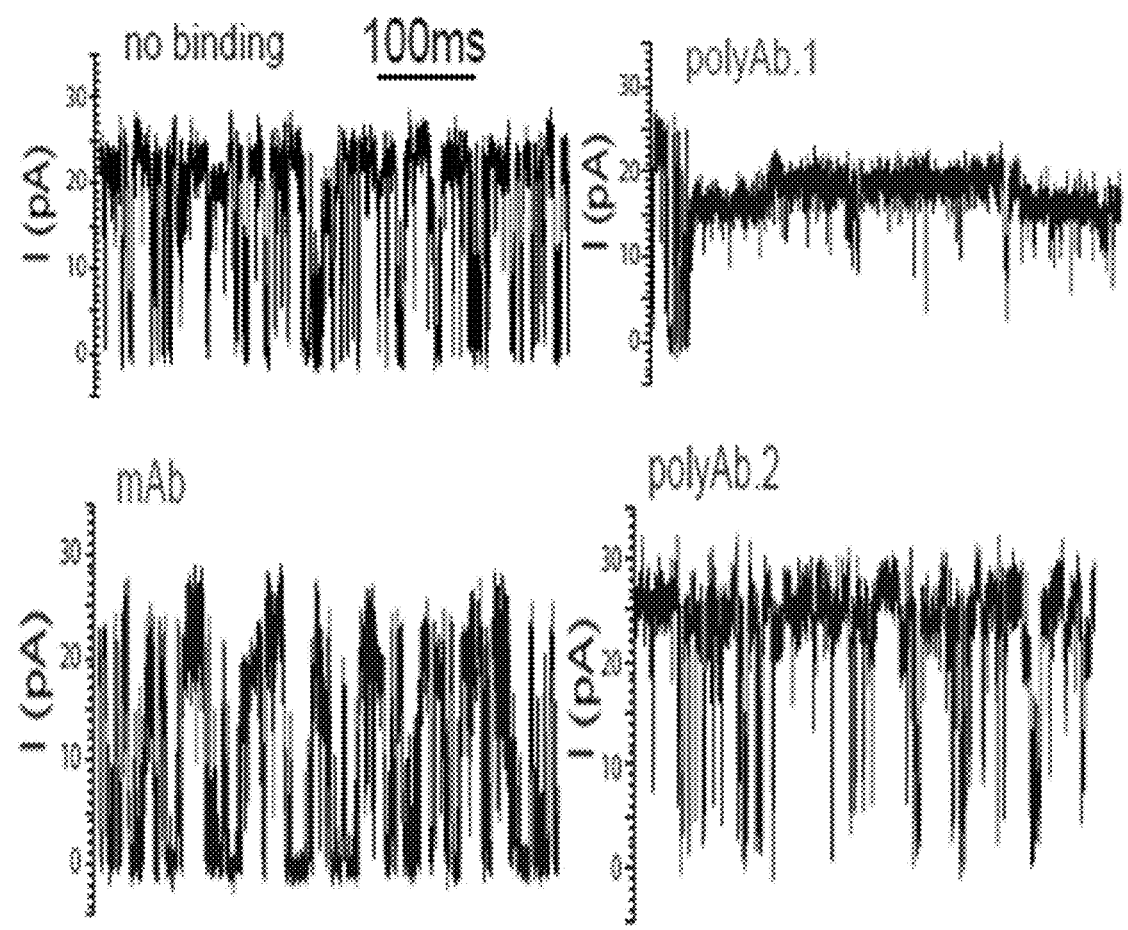
Figure 6D:
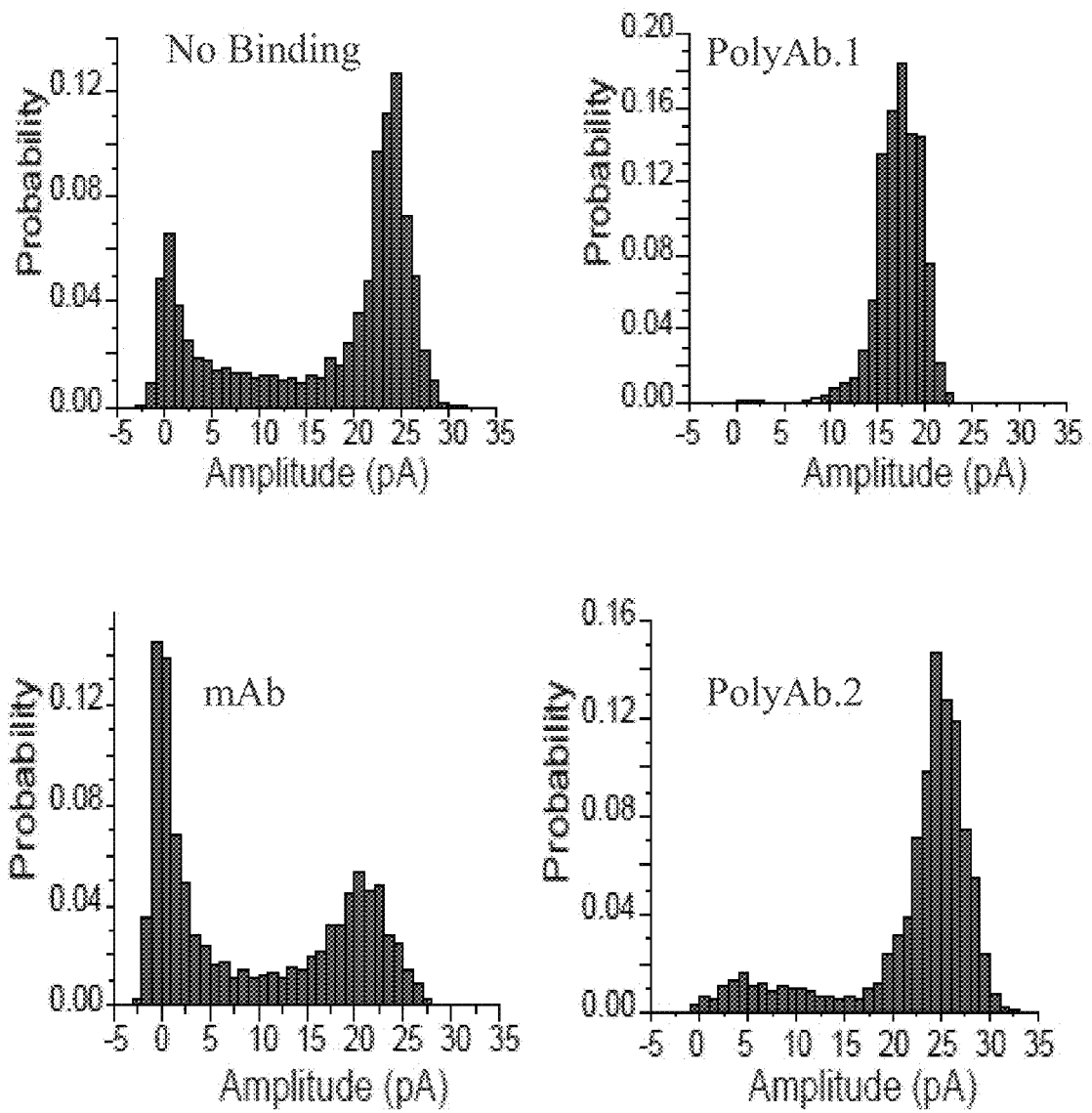

Although the antibody and streptavidin both bound the biotinylated OmpG, they produced unique gating patterns. OmpG sensor would be sensitive to various factors such as a proteins size, shape, surface charge or rigidity. In an attempt to distinguish between these, the binding of a polyclonal anti-biotin derived from goat was analyzed. The polyclonal antibody produced gating patterns distinct from the structurally very similar mAb tested earlier (FIGS. 6A, 6B). Furthermore, the polyclonal sample showed clear evidence that at least two readily distinguished populations of antibody were present (FIG. 6C). Their gating activities were categorized into two classes, called type I and type II. During type I binding (pAb.1) the current decreased by 50% and contained few gating events. During type II (pAb.2) binding events, the open state conductance was unchanged but the gating frequency was slightly reduced (FIGS. 6C, 6D). Mouse mAb was then added to the chamber already containing pAb and the binding was observed. All types of antibodies bound with their respective characteristics regardless of the presence of the other antibodies. As shown herein, nanopores are provided than can distinguish between multiple antibodies with virtually identical shape in a complex mixture.

Figure 7:
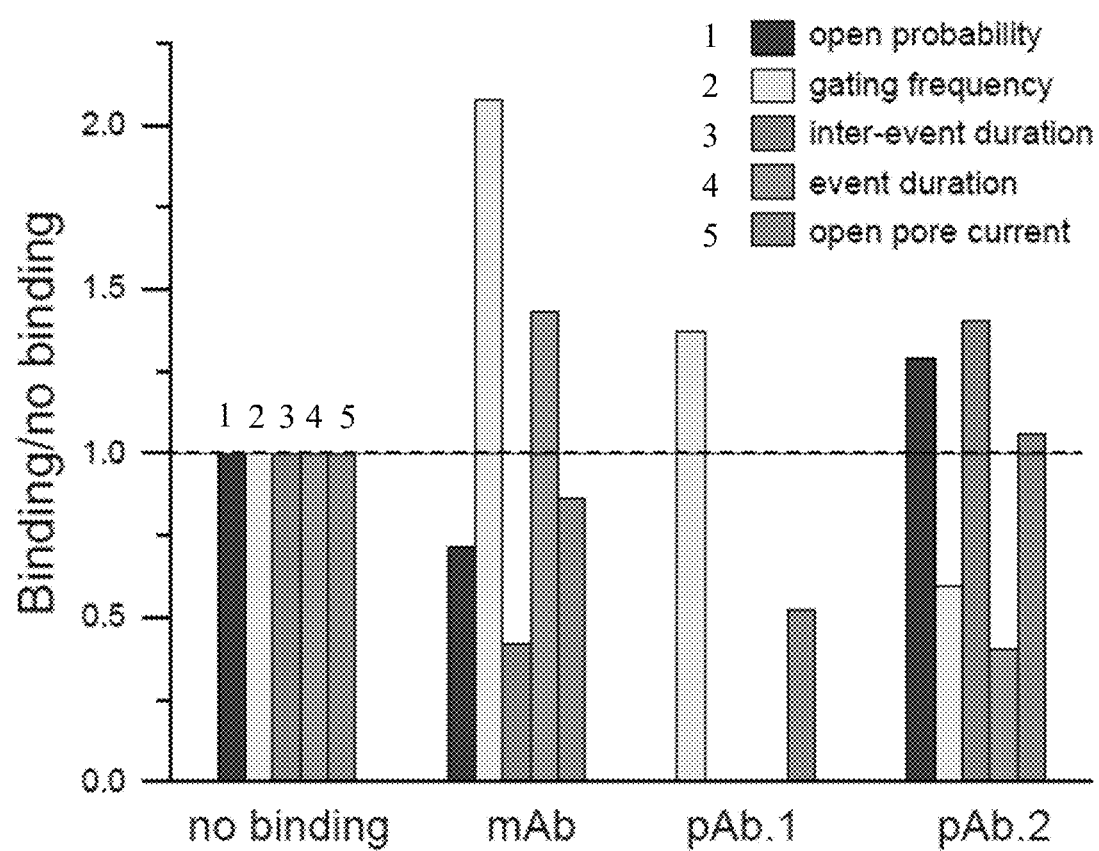
FIG. 7 depicts a comparison of the gating patterns of OmpG-PEG$_2$-biotin after binding with antibodies. The gating events of different analyte protein binding states were characterized by five parameters, i.e. open probability (1), gating frequency (2), inter-event duration (3), event duration (4) and the conductance of the open pore state (5). Changes of these parameters relative to the no binding state generate the fingerprint unique for each antibody.
Figure 8:
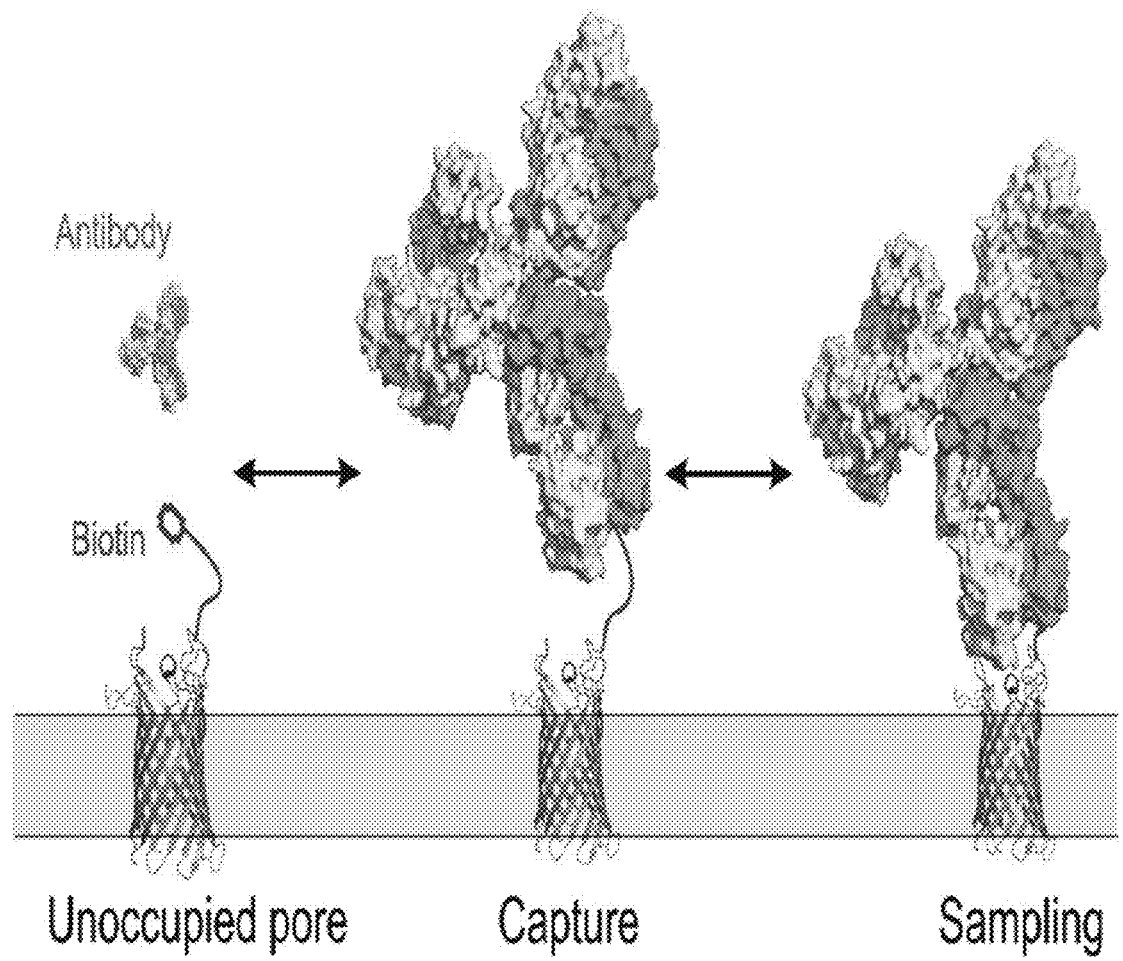
FIG. 8 depicts a schematic model illustrating the principle of OmpG nanopore detection.
Figure 9A:
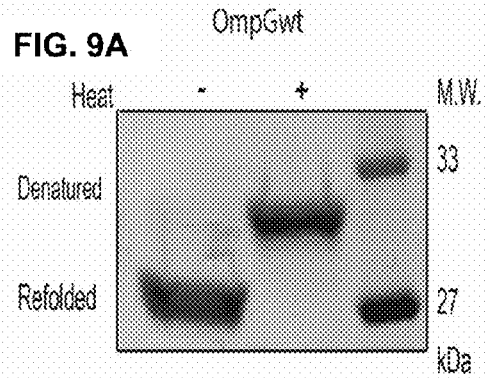
FIGS. 9A-9D show a SDS-PAGE analysis of OmpG variants. The refolded OmpG variants were either pre-heated at 95° C. for 15 min or directly loaded up to a 12.5% SDS-PAGE. Heating denatures the OmpG protein which migrates slower in SDS-PAGE. To determine the labelling efficiency, the OmpG-PEG$_{11}$-biotin and OmpG-PEG$_2$-biotin were incubated with streptavidin which forms a SDS-resistant complex with biotin. Consequently, OmpG shifts to higher-molecule weight region.
Figure 9B:
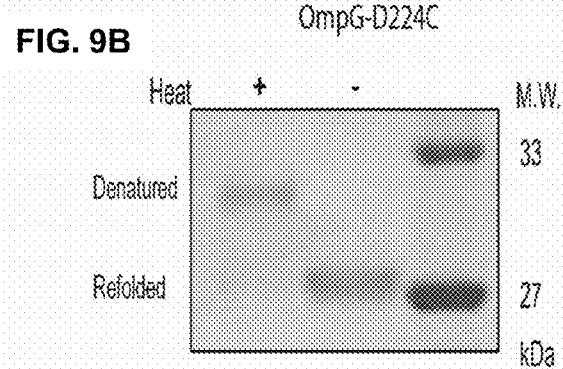
Figure 9C:
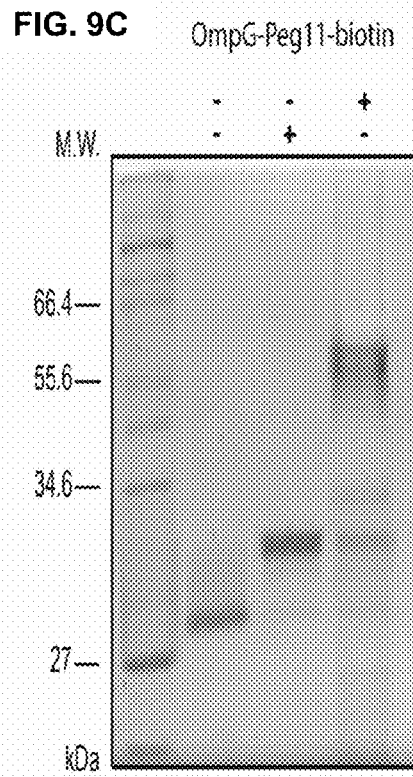
Figure 9D:
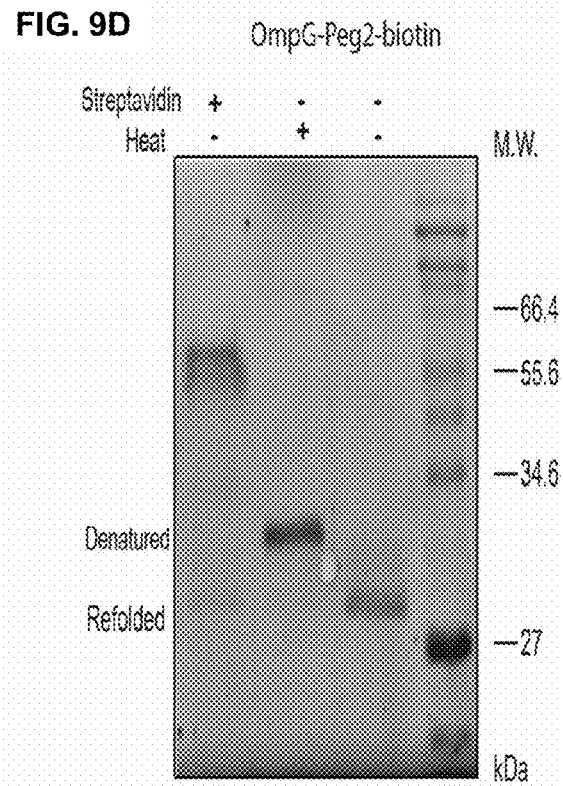
Figure 11:
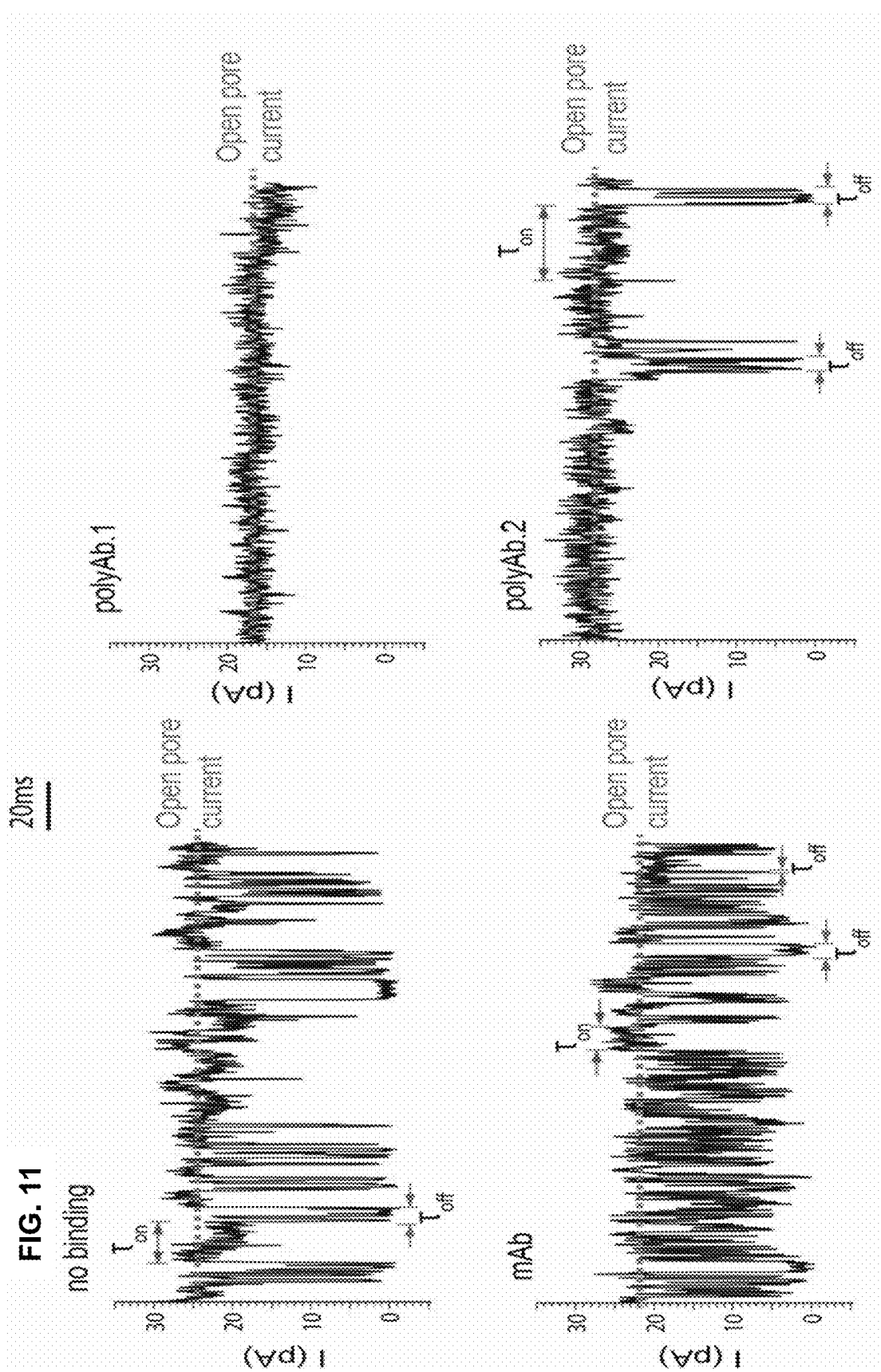
FIG. 11 shows the gating events analysis. The current recording traces were analyzed by Clampfit 10.3 using single channel search to identify gating events which were defined as current blockades larger than 2 pA (4% of fully open pore current). The open probability was calculated as the time the pore stays in the open state divided by the recording time. The gating frequency was calculated as the number gating events divided by the recording time. The average inter-event duration ($\tau_{on}$) and event duration ($\tau_{off}$) were obtained by fitting the histogram of these duration values with single exponential function the same as FIG. 10. The open pore current is indicated with a dashed line.

For each target, five parameters are analyzed: (i) open probability, (ii) gating events frequency, (iii) inter gating event duration, (iv) duration of gating events and (v) the open state conductance to identify the protein (FIG. 11). Table 1, below, summarized these parameters which provide a fingerprint for each analyte (FIG. 7). The OmpG-biotin sensor can unambiguously detect and discriminate between three antibody species (two pAb and one mAb) that share the same high-affinity ligand. Since proteins of the same size The structure of OmpG, along with the data presented here, illustrates mechanisms of protein detection via the nanopore strategy. Four biotin-binding proteins trigger a characteristic gating pattern upon binding to the OmpG nanopore. These proteins can be categorized into two groups. In pAb.2 and streptavidin cause a decreased gating frequency, which suggests binding to the PEG$_2$ tethered biotin hindered the dynamics of the loop 6. According to the crystal structure, the D224 residue traverses approximately 7.5 Å between the open and closed states. However, based on NMR analysis of OmpG, this residue may migrate as far as 30 Å between the fully open and closed conformers. In some embodiments, a large conformational change may be hindered by streptavidin binding and moderately by pAb.2 binding. In some embodiments, minimal interaction may occur between the streptavidin and pAb.2 with the loops at the opening of OmpG. In another category, mAb and pAb.1 both caused a decrease of current in the fully open state. This observation indicates that the two antibodies obstruct the current flow at the entrance, presumably by partially docking to the extracellular loops of OmpG. In some embodiments, because all seven loops at OmpG's entrance are negatively charged, the two antibodies are likely to be positively charged or have a positively charged patch near the biotin-binding site that mediate this interaction. This is consistent with the observation of mAb's asymmetrical behavior under an applied potential. Namely, in some embodiments, a positive potential might push the mAb towards the OmpG pore to cause partial block of the current. In contrast, at a negative potential, the electric field may repel the mAb away from the pore entrance. Indeed, in some embodiments, it is observed that the open pore conductance was less affected. These results indicate that not only the ligand-tethered loop, but all the loops on the extracellular entrance may be involved in sampling the target proteins, which explains its ability to discriminate between highly structurally homologous proteins. In some embodiments, the data suggests a novel mechanism underlying OmpG nanopore sensing that contains two steps (FIG. 8). First, in some embodiments, OmpG captures the target protein via its tethered high-affinity ligand. Consequently the bound protein interferes with the movement of loop 6 generating its characteristic gating pattern. Second, in some embodiments, the extracellular loops of OmpG may sample the target protein via unspecific interactions which further alters the ionic current providing additional readout. In some embodiments, the sensor's ability to discriminate between structurally homologous antibodies within a multi-component mixture represents a powerful advance over conventional approaches.

Figure 12:
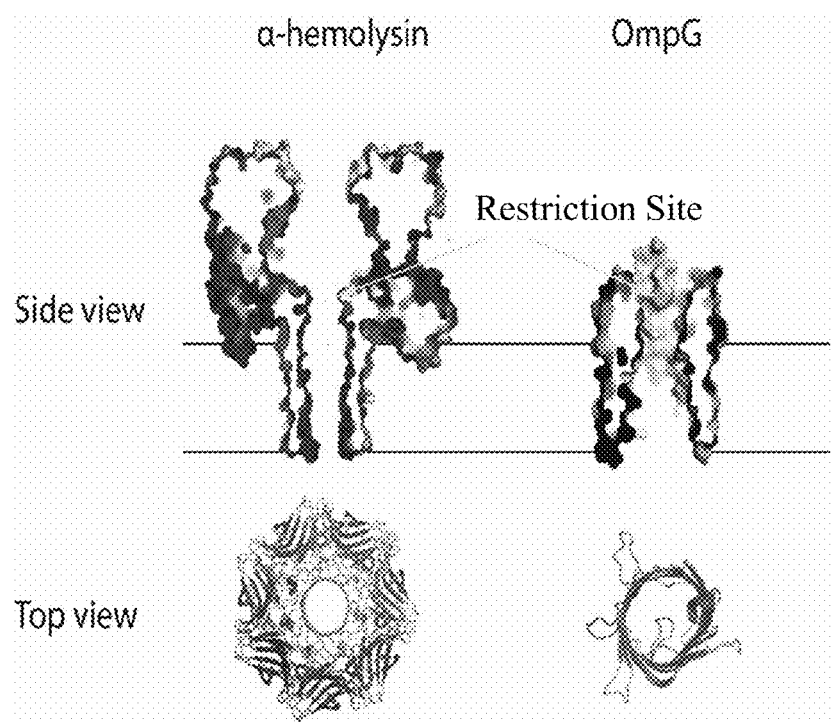
FIG. 12 depicts the structures of αHL and OmpG. The side view shows a cross-section of both proteins to reveal the restriction site. For αHL, the restriction site is located in the middle of the pore. On the contrast, the narrowest site of the pore is located at the top entrance in OmpG. The top view structures show αHL has β-strands packing into highly ordered structure at its entrance while OmpG contains seven flexible loops.

Detection of streptavidin and anti-biotin antibody has been demonstrated using αHL that contained a PEG biotin group tethered to its vestibule. In the absence of the target, the PEG polymer traversed through the restriction site from the cis and trans chamber and back through the pore. This movement was manifest as rapid gating. Analyte protein binding of the biotin group eliminated the gating and provided the readout signal for protein sensing. In contrast to the OmpG nanopore, αHL-biotin sensor did not differentiate binding events derived from streptavidin and mAb which differ greatly in size, shape and surface properties. In some embodiments, two features of OmpG may contribute to its higher resolution compared to αHL (FIG. 12). The first is the location of the restriction site which is the narrowest part of the pore that determines the conductance. The restriction site of OmpG-PEG$_2$-biotin is located at the entrance to the pore next to the ligand interaction site while the location of the restriction site of αHL is in the middle making it inaccessible for analyte protein. Because of this, analyte protein binding at the pore entrance directly affected the conductance of OmpG but not αHL. Secondly OmpG has flexible loops at the binding site which allows conformational changes to occur in response to analyte protein binding. Instead, αHL possesses a rather stable and rigid structure at the two ends. Although the biotin-binding proteins might also interact with the two entrances of αHL nanopore, the rigidity of the αHL structure does not allow large conformational changes to occur, so the interaction of different target proteins with the entrance did not induce noticeable changes in the current flow that passed through the restriction site.

By creating a nanopore with a dynamic structure that changes upon analyte binding, new regions of data may be interpreted that give a greater sensitivity and selectivity for detecting protein analytes. It has been shown that even protein isoforms in a mixture can be clearly distinguished using this new sensing scheme. These features are not available in conventional nanopore sensing strategies, making the OmpG sensor and other monomeric sensors particularly useful. Further, monomeric proteins such as OmpG are ready to use after refolding and require no further assembly and purification steps compared to other oligomeric nanopores.

These studies have shown that binding of target protein to an OmpG-biotin nanopore can be deduced from changes in the gating activity of OmpG. The principle of the OmpG nanopore involves detecting the modulation of loop dynamics upon target protein binding rather than the occupation in the pore lumen. Moreover, the OmpG nanopore exhibited the ability to resolve protein homologues that share the same high-affinity ligand, making this sensing approach well suitable for screening for homologous disease markers. Accordingly, the sensors are useful for a broader spectrum of analytes, such as proteins, viruses, or bacteria without the need to use a far larger nanopore.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A composition comprising:
an outer membrane protein G (OmpG) of *E.coli* origin disposed in a membrane preparation, the outer membrane protein comprising fourteen β-strands connected by seven flexible loops on a first side of the membrane preparation and seven short turns on a second side of the membrane preparation, wherein a cysteine is substituted for an aspartic acid at amino acid position 224 present in loop 6 of the plurality of flexible loops, and wherein a non-natural, engineered binding site for a target molecule is covalently tethered to the single cysteine; and
the target molecule.

2. A composition comprising:
an outer membrane protein G (OmpG) of *E.coli* origin disposed in a membrane preparation, the outer membrane protein comprising fourteen β-strands connected by seven flexible loops on a first side of the membrane preparation and seven short turns on a second side of the membrane preparation, wherein a cysteine is substituted for an amino acid of SEQ ID NO: 7, which is an amino acid sequence of loop 6 of the plurality of flexible loops of the OmpG protein, wherein a non-natural, engineered binding site for a target molecule is covalently tethered to the cysteine.

3. The composition of claim 2, wherein the cysteine is substituted for an aspartic acid at amino acid position 224.

4. The composition of claim 2, wherein the outer membrane protein comprises on a first side of the membrane an opening in a range of 6 to 10 Å in diameter and an opening on a second side of the membrane in a range of 12 to 16 Å.

5. The composition of claim 2, wherein at least one of the flexible loops is stabilized to reduce gating.

6. The composition of claim 2, wherein the cysteine is substituted for an aspartic acid at amino acid position 221.

7. The composition of claim 2, wherein the aspartic acid is at position 224 of the OmpG.

8. The composition of claim 2, wherein a ligand of a target molecule is covalently tethered to the cysteine.

* * * * *